(12) United States Patent
Heinje et al.

(10) Patent No.: US 9,792,416 B2
(45) Date of Patent: Oct. 17, 2017

(54) PEAK CORRELATION AND CLUSTERING IN FLUIDIC SAMPLE SEPARATION

(75) Inventors: Gerd Heinje, Waldbronn (DE); Rainer Jaeger, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 1169 days.

(21) Appl. No.: 13/252,731

(22) Filed: Oct. 4, 2011

(65) Prior Publication Data

US 2012/0116689 A1    May 10, 2012

(30) Foreign Application Priority Data

Nov. 4, 2010  (GB) .................................. 1018608.8

(51) Int. Cl.
*G06F 19/00* (2011.01)
*G06T 11/20* (2006.01)

(52) U.S. Cl.
CPC .......... *G06F 19/707* (2013.01); *G06F 19/708* (2013.01); *G06T 11/206* (2013.01)

(58) Field of Classification Search
CPC ............... G01N 30/7233; G01N 30/86; G01N 30/8617; G01N 2030/0035; G01N 2030/0065; G01N 2030/007; G01N 30/0005; H01J 49/0036
See application file for complete search history.

(56) References Cited

U.S. PATENT DOCUMENTS

| | | | |
|---|---|---|---|
| 5,606,164 A * | 2/1997 | Price et al. ............... | 250/339.09 |
| 2006/0020401 A1* | 1/2006 | Davis et al. .................... | 702/30 |
| 2006/0055945 A1 | 3/2006 | Fazakerly | |
| 2009/0294645 A1* | 12/2009 | Gorenstein et al. .......... | 250/282 |

FOREIGN PATENT DOCUMENTS

| | | |
|---|---|---|
| DE | 102007000627 A1 | 5/2009 |
| WO | 0028573 A2 | 5/2000 |
| WO | 2005106920 A2 | 11/2005 |

OTHER PUBLICATIONS

Great Britain Search Report dated Mar. 3, 2011.
Niels-Peter Vest Nielsen et al., Aligning of single and multiple wavelength chromatographic profiles for chemometric data analysis using correlation optimised warping, Journal of Chromatography A, vol. 805, Issues 1-2, May 1, 1998, pp. 17-35, Elsevier Science B.V.

* cited by examiner

*Primary Examiner* — Gregory J Toatley
*Assistant Examiner* — Kyle R Quigley

(57) ABSTRACT

A device for analyzing measurement data having a plurality of data sets, each data set being assigned to a respective one of a plurality of measurements, each data set having multiple features being indicative of different fractions of a fluidic sample, the device comprising a cluster determining unit configured for determining feature clusters by clustering features from different data sets presumably relating to the same fraction, a spread determining unit configured for determining for at least a part of the feature clusters a spread of the features within a respective feature cluster, and a display unit configured for displaying at least the part of the feature clusters together with a graphical indication of the corresponding spread.

25 Claims, 13 Drawing Sheets

PEAK CORRELATION AND CLUSTERING IN FLUIDIC SAMPLE SEPARATION

CROSS-REFERENCE TO RELATED APPLICATIONS

This application claims priority under 35 U.S.C. §119(e) from Great Britain Patent Application, No. GB 10186088 filed on 4 Nov. 2010, which is incorporated by reference in its entirety.

BACKGROUND

The present invention relates to a data analysis system.

Measurement instruments are applied to execute various measurement tasks in order to measure any kind of physical parameter. As a result of a measurement, measurement data is output by the measurement instrument. Such measurement data may include values of physical parameters such as concentrations of components of a sample, intensity values of a fluorescence measurement, etc. This information can be displayed to a user via a graphical user interface for evaluation of the data.

An example for such a measurement instrument is a coupled liquid chromatography and mass spectroscopy device (for instance the 1200 Series LC/MSD of Agilent Technologies).

DE 10 2007 000 627 A1 discloses a device which has a processing unit, e.g. CPU, for processing of measured data of a liquid chromatography measurement and mass spectrometer measurements such that the processed data are represented in two dimensions. Parameters such as retention time and mass spectrometer-spectrum and characterizing the measurements are represented in dimensions, where the latter parameter is correlated with the former parameter. The processing unit is arranged such that data of an original sample, i.e. fluid sample, and data of fragments of the sample are represented in two dimensions.

Niels-Peter Vest Nielsen, Jens Michael Carstensen, Jon Smedsgaard, "Aligning of single and multiple wavelength chromatographic profiles for chemometric data analysis using correlation optimized warping", Journal of Chromatography A, 805 (1998) 17-35, discloses that the use of chemometric data processing is becoming an important part of modern chromatography. Most chemometric analyses are performed on reduced data sets using areas of selected peaks detected in the chromatograms, which means a loss of data and introduces the problem of extracting peak data from the chromatographic profiles. These disadvantages shall be overcome by using the entire chromatographic data matrix in chemometric analyses, but it is necessary to align the chromatograms, as small unavoidable differences in experimental conditions cause minor changes and drift. The method uses the entire chromatographic data matrices and does not require any preprocessing, e.g. peak detection. It relies on piecewise linear correlation optimized warping (COW) using two input parameters which can be estimated from the observed peak width. COW is demonstrated on constructed single trace chromatograms and on single and multiple wavelength chromatograms obtained from HPLC diode detection analyses of fungal extracts.

WO 2005/106920 discloses a method of mass spectrometry which comprises determining a first physico-chemical property and a second physico-chemical property of components, molecules or analytes in a first sample, wherein said first physicochemical property comprises the mass or mass to charge ratio and said second physico-chemical property comprises the elution time, hydrophobicity, hydrophilicity, migration time, or chromatographic retention time. A first physico-chemical property and a second physico-chemical property of components, molecules or analytes in a second sample is determined, wherein said first physico-chemical property comprises the mass or mass to charge ratio and said second physico-chemical property comprises the elution time, hydrophobicity, hydrophilicity, migration time, or chromatographic retention time. Data relating to components, molecules or analytes in said first sample is probabilistically associated, clustered or grouped with data relating to components, molecules or analytes in said second sample.

For the management of such measurement data, a user interface may be appropriate for visualizing corresponding data items to a user in a way that a technically reasonable evaluation of the measurement data is enabled. In this respect, conventional data analysis systems may be inconvenient in use.

SUMMARY

It is an object of the invention to provide a convenient data analysis system simplifying a technically reasonable evaluation of the measurement data for a user.

According to an exemplary embodiment, a device for analyzing measurement data having a plurality of data sets is provided, each data set being assigned to a respective one of a plurality of measurements, each data set having multiple features being indicative of different fractions of a fluidic sample (particularly of a fluidic sample to be separated by a respective one of the plurality of measurements), the device comprising a cluster determining unit configured for determining feature clusters by clustering features from different data sets presumably relating (or assumed to relate) to the same fraction, a spreading determining unit configured for determining for at least a part of the feature clusters a spreading of the features within a respective feature cluster, and a display unit configured for displaying at least the part of the feature clusters together with a graphical indication of the corresponding spreading.

According to another exemplary embodiment, a method of analyzing measurement data having a plurality of data sets is provided, each data set being assigned to a respective one of a plurality of measurements, each data set having multiple features being indicative of different fractions of a fluidic sample, wherein the method comprises determining feature clusters by clustering features from different data sets relating to the same fraction, determining for at least a part of the feature clusters a spreading of the features within a respective feature cluster, and displaying at least the part of the feature clusters together with a graphical indication of the corresponding spreading.

According to an exemplary embodiment, a device for processing measurement data having a plurality of data sets is provided, each data set being assigned to a respective one of a plurality of measurements, each data set having multiple features being indicative of different fractions of a fluidic sample, wherein each feature represents a combination of a value of a first measurement parameter with a value of a second measurement parameter, the device being configured for determining feature clusters by clustering features from different data sets presumably relating (or assumed to relate) to the same fraction by ordering at least a part of the features in accordance with the value of the first measurement parameter, and determining the feature clusters by clustering features to a respective feature cluster which fulfill the condition that a difference regarding the value of the first measurement parameter between adjacent features of a feature cluster in the ordered representation is below a predetermined threshold value (particularly clustering all features to a respective feature cluster which fulfill the mentioned condition under consideration of the boundary condition that not more than one feature of a respective data set forms part of the same feature cluster).

According to another exemplary embodiment, a method of processing measurement data having a plurality of data sets is provided, each data set being assigned to a respective one of a plurality of measurements, each data set having multiple features being indicative of different fractions of a fluidic sample, wherein each feature represents a combination of a value of a first measurement parameter with a value of a second measurement parameter, wherein the method comprises determining feature clusters by clustering features from different data sets relating to the same fraction by ordering at least a part of the features in accordance with the value of the first measurement parameter, and determining the feature clusters by clustering features to a respective feature cluster which fulfill the condition that a difference regarding the value of the first measurement parameter between adjacent features of a feature cluster in the ordered representation is below a predetermined threshold value.

According to still another exemplary embodiment of the present invention, a software program or product is provided, preferably stored on a data carrier, for controlling or executing any of the methods having the above mentioned features, when run on a data processing system such as a computer.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in the context of measurement data analysis. The measurement data analysis scheme according to an embodiment of the invention can be performed or assisted by a computer program, i.e. by software, or by using one or more special electronic optimization circuits, i.e. in hardware, or in hybrid form, i.e. by means of software components and hardware components.

In the context of this application, the term "measurement data" may particularly denote experimental data obtained from a measurement regarding a sample comprising multiple fractions or components which are to be separated from one another. For example, such measurement data may be liquid or gaseous chromatography data.

The term "data set" may particularly denote a portion of the measurement data, more precisely experimental data which relate to one and the same measurement on one and the same fluidic sample. For instance, multiple measurements may be performed with multiple physically different samples, whereas the samples are preferably treated under same or comparable measurement conditions. Hence, each data set may correspond to a respective one of several experimental runs on a measurement device for separating a corresponding fluidic sample in the different fractions. It is possible to use different samples, one for each measurement relating to a corresponding data set. In another embodiment, it is possible to use the same sample and run the same experiment multiple times to capture various data sets together forming the measurement data.

The term "feature" (more particularly signal feature) may particularly denote a characteristic subsection in a measurement signal which has a special shape, value, etc., which distinguishes the subsection from surrounding portions. When referring to a "signal feature", "signal" should be understood as relating to a measurement signal of any type such as a chromatogram. For example, such a feature may be a peak, a dip, a step or the like in the signal with a dedicated pattern being indicative of a certain measurement event.

The term "fractions of a fluidic sample" may particularly denote different components (such as different chemical compounds) of a fluidic sample, i.e. of a gaseous and/or liquid sample. For example, different genes or different proteins in a biological sample can form the different fractions. By a fluid separation method performed by the measurement device, it is possible to physically and spatially separate the different fractions of the fluidic sample, for instance by liquid or gaseous chromatography or gel electrophoresis.

The term "presumably relating to the same fraction" (or assumed to relate to the same fraction) may reflect the fact that the evaluation scheme considers features to relate to the same fraction in the case of certain circumstances, for instance if one or more decision criteria is or are fulfilled. Such a decision criterion may be that clustered features of a respective feature cluster fulfill the condition that a difference regarding a value of a measurement parameter between adjacent features of a feature cluster in an ordered representation is below a predetermined threshold value. Another decision criteria may be that a result of the application of a recursive algorithm results in that certain features in fact relate to the same fraction. Since however, for instance in the presence of artifacts in the measurement signal, it cannot be ruled out completely that the evaluation scheme erroneously assigns a certain feature to a certain fraction under undesired circumstances, an assignment will be denoted here a presumable relation to the same fraction.

The term "feature cluster" may particularly denote a group of two, three, four or more features relating to different measurements and therefore data sets, but apparently relating to the same fraction, e.g. physical, chemical or biochemical component. For simplifying evaluation of multiple measurements with multiple fractions of a fluidic sample for a user, the clustering of the features may visually ease the understanding which of the features relate to one another in a physical sense.

The term "spread of the features" (which may also be denoted as "spreading of the features", "cluster bandwidth of the features", "distribution of the features") may particularly denote a deviation or variation of the features among a feature cluster regarding a certain measurement parameter. Such a spread may be any statistical measure (particularly a reliability value) indicative of to which quantitative amount the individual features of a cluster presumably relating to the same fraction differ from measurement to measurement. Hence, the spread gives a quantitative measure for the degree of reliability of the clustering.

The term "graphical indication" may particularly denote any visualization of the correlation between the individual features of a feature cluster on the one hand and their spread on the other hand. The graphical indication shall make clear to a user how large the uncertainty of the grouping is. A large spread usually corresponds to a lower certainty or reliability of the feature grouping as compared to a small spread.

The term "value of a measurement parameter" may particularly denote a quantitative value of a measured parameter in a certain measurement. Which measurement parameter is analyzed depends on the kind of measurement being performed.

The term "adjacent features of a feature cluster in an ordered representation" may particularly denote that firstly, the features may be quantitatively ordered after a projection on a measurement parameter axis (particularly from small values to larger values), and secondly, direct neighbors in the quantitative order are regarded. In a corresponding one-dimensional representation of these features, it is possible to compare neighbored or adjacent features with regard to their distance from one another in terms of the (first) measurement parameter. Hence, the smallest and the second smallest feature are considered adjacent, the second smallest and the third smallest, . . . , and the second largest and the largest feature are considered adjacent. Thus, directly neighbored features (particularly all pairs of directly neighbored features) are pairwise compared (by a subtraction operation) with regard to the difference concerning the first measurement parameter.

According to a first aspect, a technical assistance system is provided for a technician such as an engineer, a chemist or a biologist which takes a technically well-founded approach for a grouping of different signal features into corresponding clusters. Particularly the occurrence of features at basically the same position on a measurement axis is considered as a clear indication for the assumption that they relate to the same separation/measurement conditions. However, since it cannot be ruled out that such an algorithm-based clustering of potentially defective measurement data maintains the risk of a false clustering, a spread indicative of the reliability of this machine-based clustering is calculated and displayed to the user in combination with the result of the clustering. Therefore, a visual indication is given to the user indicative of the reliability of the clustering performed by the system. Therefore, the technically skilled user is assisted to properly evaluate multiple features in multiple measurements, but at the same time the system clearly gives the user an indication with regard to the amount of technical uncertainty of the clustering. Therefore, it can be safely prevented that the technician simply accepts the clustering of the machine as always correct, and hence technically meaningful information is provided to the user as to whether the estimation is reliable to a very high degree or to a lower degree.

According to a second aspect, an accurate and numerically simple algorithm for clustering is provided which allows to cluster features with reasonable computational burden and therefore in a very fast manner for forming feature clusters in an intuitive and technically well-grounded manner. For this purpose, a simple ordering scheme is applied which orders the clusters of the multiple measurements in accordance with a quantitative ordering criteria, for instance in ascending order or in descending order. Particularly, it is not necessary to perform a numerically complex, time-consuming recursive algorithm for the clustering, but in contrast to this a simple comparison of the distance of (or difference between) adjacent pairs of features in terms of the first measurement parameter is sufficient. It is simply checked whether the distance of the value of the measurement parameter between adjacent features is larger or smaller than a predefined threshold value. On the basis of this estimation, a reliable clustering can be performed which has turned out to be properly reliable and which can avoid artifacts to a large extent.

In the following, further exemplary embodiments of the devices will be explained. However, these embodiments also apply to the methods and to the software program or product.

In an embodiment, each feature represents a combination of a value of a first measurement parameter with a value of a second measurement parameter. The cluster determining unit may be configured for ordering at least a part of the features in accordance with the value of the first measurement parameter, particularly ordering from small to large values, and determining the feature clusters by clustering features to a respective feature cluster which fulfill the clustering condition that a difference regarding the value of the first measurement parameter between each adjacent features of a feature cluster in the ordered representation is below a predetermined threshold value. In this context, "each" means that all features of a group are clustered to one cluster, in which group the condition is pairwise fulfilled that each two neighbors in the ordered representation have a distance in terms of the value of the first measurement data of less than the predetermined threshold value. This a very simple algorithm which provides surprisingly reliable results.

In an embodiment, the predetermined threshold value is a time interval indicative of a difference regarding a retention time of a corresponding fraction in different ones of the measurements. The retention time can be defined as a parameter in chromatography which corresponds to the elapsed time between the time of injection of a sample or solute and the time of elution of the peak maximum of a fraction of that sample or solute. Hence, the retention time is a unique characteristic of the fraction in the solute and can be used for identification purposes. The value of the predetermined threshold value may for instance be estimated using expert knowledge, i.e. empirical information regarding liquid or gaseous chromatography being indicative of the variation of the retention time (or alternatively the retention volume) in different measurements.

In an embodiment, the predetermined threshold value is a time interval within a range from about 0.001 minutes to about 0.1 minutes, particularly within a range from about 0.005 minutes to about 0.08 minutes. It turns out that the provided values are very suitable to ensure a proper clustering, particularly when the predetermined threshold value is between 0.01 minutes to 0.03 minutes.

In an embodiment, the cluster determining unit is configured for determining the feature clusters using a non-recursive algorithm. Recursion may be denoted as a method of defining functions in which a function being defined is applied within its own definition. Thus, recursion implies an iterative approach with a relatively high computational burden. In contrast to this, exemplary embodiments of the invention rely on a simple pairwise comparison of adjacent measurement values which does not need recursions and is therefore less prone to a high consumption of processing capacity.

In an embodiment, the cluster determining unit is configured for excluding a feature from a feature group (i.e. for not including this feature in a cluster) upon determining that this feature has a value of the first measurement parameter which is larger than a value of the first measurement parameter of another feature of the same data set by less than another predetermined threshold value, i.e. a further threshold value which can be considered as a parameter which is separate from the above mentioned threshold value determining whether different features of different data set should be considered to relate to the same cluster. In an embodiment, the cluster determining unit is configured for determining the feature clusters by clustering all features to a respective feature cluster which fulfill the clustering condition among each other under consideration of the boundary condition that at most one feature per data set may form part of the same feature cluster. Hence, according to such embodiments it shall be ruled out that a feature cluster includes multiple features from the same measurement, because different distinguishable features in the same measurement are considered as a clear technical indication for two different fractions, thereby contravening the assumption that features of a cluster relate to the same fraction. Hence, if two features relating to the same data set are closer to one another than the other predetermined threshold value, the second fraction in the ordered list will not be allowed to form part of the cluster in the described embodiment. The other predefined threshold value is preferably the same threshold value as the one used for determining whether two features of different data sets relate to the same cluster or not. However, the values may also be different from one another, if desired or required.

In an embodiment, the cluster determining unit is configured for determining whether a first (for instance having the smallest value of the first parameter) and a last (for instance having the largest value of the first parameter) of the features in the ordered representation of a feature cluster differ regarding the value of the first measurement parameter by more than a predetermined further threshold value, and for triggering a predefined action upon determining that the predetermined further threshold value is exceeded. Under undesired circumstances, it can happen that all adjacent features of a cluster fulfill the above-mentioned threshold value condition, but nevertheless the distance between the features of a cluster as a whole is too large to reasonably assume from a technical point of view that the cluster features really relate to the same fraction. Therefore, if a further threshold value which is usually larger than the before mentioned threshold values is exceeded, it will not be assumed in the described embodiment that all the features of the determined cluster relate to the same fraction. For this reason, a corresponding action may be triggered when this criteria is met. This action may for instance be an alarm alarming a user that the clustering is probably not reliable. The action may however also be that the clustering algorithm will not be applied for clustering and no or another clustering algorithm has to be applied, for instance a recursive clustering algorithm.

In an embodiment, the display unit is configured for displaying a bar having a width corresponding to the respective spread as the graphical indication. A bar is a clear visual indicator showing to a human user in a very intuitive manner how reliable the clustering has been. A bar structurally connects all cluster features visually and therefore gives a further visual indication for the clustering result. However, as an alternative to a bar, it is also possible to use for instance a line of a corresponding length, a color code or a numerical indication of the spread. By such an illustration of the clustering in connection with the two measurement parameters in a coordinate system, it can be possible for a user with one view to understand which clusters have been formed.

In an embodiment, each feature represents a combination of a value of a first measurement parameter with a value of a second measurement parameter. The display unit may be configured for displaying a coordinate system having a first dimension along which the value of the first measurement parameter is displayable for at least a part of the features and having a second dimension along which at least a part of the data sets is displayable for at least a part of the features. The value of the second measurement parameter for at least a part of the features is displayable in a manner such that the value is encoded by a graphical property of a respective marker in the coordinate system. Hence, the display of the second measurement parameter does not necessarily require a separate coordination axis, since its value can be encoded as a property of marker.

In an embodiment, the coordinate system is a Cartesian coordinate system. Alternatively, other two dimensional coordinate systems are possible. Also a three- or more-dimensional coordinate system may be used. However, the use of a Cartesian coordinate system makes the visual confirmation and approval of a clustering by a user very easy, since the uncertainty connected with the clustering can be easily derived visually from a Cartesian coordinate system.

In an embodiment, the graphical property is a size of the marker, particularly an area of a circular marker. For example, the larger the value of the second measurement value, the larger the area. Hence, the area of such a circular marker can be used as an indication how large the feature was in the original measurement signal, for instance which area a corresponding peak of a liquid or gaseous chromatography measurement has. However, it is also possible to use additionally or alternatively other indicators than the size of the marker—for instance a color—for indicating the value of the second measurement parameter.

In an embodiment, the first parameter is indicative of a retention time (or a retention volume) of a chromatography measurement, or a mass to charge ratio of a coupled liquid chromatography and mass spectroscopy measurement. However, these parameters are only exemplary, since other parameters may be used when other kinds of measurements are carried out.

In an embodiment, the second parameter is indicative of a detection intensity of a peak of a chromatography measurement. Again, also the second parameter may be different from the detection intensity when other measurements are carried out.

In an embodiment, the display unit is configured for displaying the graphical indication in an overlaying manner with the markers of the features of the corresponding feature cluster. By visually projecting the graphical indication with the markers of the features in a coordinate system, it is easy for a user to verify which features relate to the same cluster and how large the spread of the individual features within a cluster is.

In an embodiment, the second dimension is a vertical coordination axis on a display. The display unit may be configured for displaying the graphical indication extending along the vertical coordination axis. By drawing a bar along a vertical coordination axis, it is easy for a user to check the distribution of the clusters within the bar extending along such a vertical coordination axis but relating to different measurements. Therefore, this makes the evaluation of the measurement even more intuitive.

In an embodiment, the device comprises a fraction identification unit configured for identifying individual fractions assigned to features in different data sets by determining a match with preknown technical information. The cluster determining unit may be configured for determining feature clusters by clustering exclusively features which have not been assigned to individual fractions by the fraction identification unit. Such a fraction identification unit can be configured in a conventional manner, since it is known to the skilled person for instance in the art of liquid or gaseous chromatography as to how a fraction is identified from a measurement signal. Usually, certain fractions of a fluidic sample to be separated are expected at certain retention times, so that the retention time, the intensity of the corresponding measurement peaks or other features can be used for fraction identification. However, it is also possible in a liquid or gaseous chromatography measurement or another measurement, that certain features cannot be identified or assigned unambiguously or with a sufficient reliability to a certain fraction. In this case, exclusively these non-identified features can be made subject to the clustering algorithm of embodiments of the invention, whereas identified clusters need not to go through the clustering algorithm. Therefore, the technically clear cases need no clustering, but only the peaks which are difficult to assign are clustered to make the evaluation easier for the user. For instance, the clustering may be performed only for non-identified peaks which can relate to impurities which occur in the sample or the like.

In an embodiment, the device may be configured as a graphical user interface (GUI) which may be denoted as a user interface which allows people to interact with electronic devices such as computers or handheld devices. A GUI offers graphical icons and visual indicators as opposed to purely text based interfaces, typed command labels or text navigation to fully represent the information and actions available to a user. The actions may then be performed through direct manipulation of the graphical elements. Therefore, a user may input preferences to make clustering appropriate for her or his purposes. For instance, the various threshold parameters may be input by a user, therefore allowing to adjust the clustering to the needs of a user. Alternatively, the system can be fully automatic, or it can be a combination of an automatic and a user-defined clustering and spread estimation.

In an embodiment, the measurement data comprises liquid or gaseous chromatography data. In one embodiment, the measurement data comprises coupled liquid chromatography and mass spectroscopy data. In an embodiment, the measurement data is provided by a measurement device which comprises at least one of a sensor device, a test device for testing a device under test or a substance, a device for chemical, biological and/or pharmaceutical analysis, a fluid separation system configured for separating compounds of a fluid, a capillary electrophoresis device, a liquid chromatography device, a gas chromatography device, an electronic measurement device, and a mass spectroscopy device. However, other applications and kinds of measurements are possible as well.

The device may be adapted for processing a displayed two-dimensional set of data, and particularly may be adapted for processing a measurement curve. Such a measurement curve may be provided by a measurement apparatus, for instance a life science apparatus or any other technical apparatus. Evaluating such measurement data may be conventionally a challenge and may be significantly simplified by the intuitive user interface according to an exemplary embodiment. However, in other embodiments, it is also possible to display three or more-dimensional data.

By clustering, accumulations of features relating to the same species of a sample, particularly a biochemical sample, may be identified. Hence, a user interface particularly for liquid or gaseous chromatography and mass spectroscopy technology may be provided, wherein a number of measurement diagrams or spectra are taken from various different measurements. Then, it is identified from this which peaks correspond to one another. Due to slightly varying experimental conditions in the various measurements, a change or variation in the sample, or change of other parameters such as solvent and/or temperature may result in a slight shifting of various features or peaks in different data sets although these peaks relate to the same fraction, species or chemicals.

Identifying and assigning peaks relating to the same cluster is then important for purposes of reproducibility, which is particularly important in pharmacology and related technologies. A measure for the spread which is then estimated can for instance be the variance or a standard deviation. It may alternatively be a distance between centers of the features on the lower limit and the upper limit of a cluster.

Hence, embodiments of the invention relate to a system of correlating any desired measurement value in a row of repeated measurements. Result of the correlation is the classification of the measured values at the individual measurements in terms of clusters. An exemplary application of an embodiment of the invention is the purity control of synthesized products, for instance in pharmacology. In this example, the repeated measurements may be chromatograms of different samples from one batch or multiple batches producing the same product. The measurement value as a basis for the clustering is the retention time of non-identified peaks. The result of the correlation are clusters of peaks from the various chromatograms with nearly identical retention time, i.e. retention times differing only within a retention time window. In this example, the clusters can be considered as unknown components such as impurities which have been introduced in the sample (for instance components which should not occur at an optimum processing or only in very small amounts). The diagram then allows to identify such peaks showing unexpected fractions. The clustering then allows for a more detailed understanding of the characteristics of the peak.

BRIEF DESCRIPTION OF THE DRAWINGS

Other objects and many of the attendant advantages of embodiments of the present invention will be readily appreciated and become better understood by reference to the following more detailed description of embodiments in connection with the accompanying drawings. Features that are substantially or functionally equal or similar will be referred to by the same reference signs.

Figure 1:
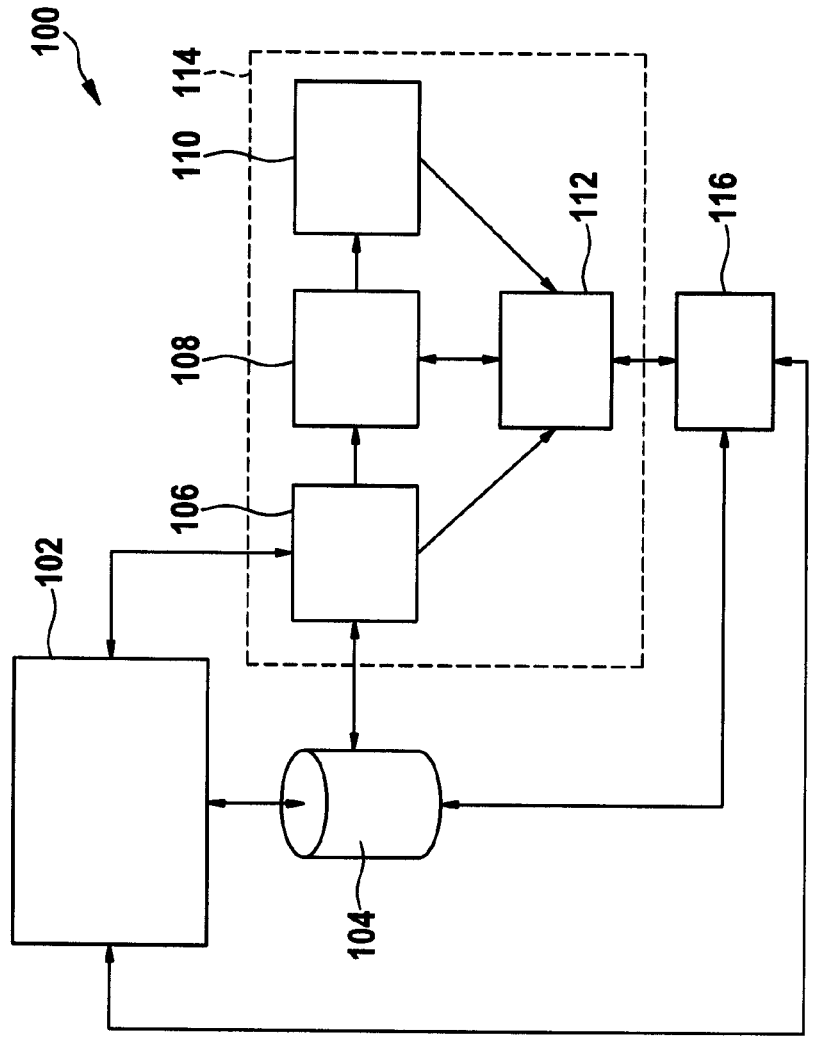
FIG. 1 shows a device for analyzing measurement data having a plurality of data sets according to an exemplary embodiment of the invention.

The illustration in the drawing is schematic.

DETAILED DESCRIPTION

Figure 24:
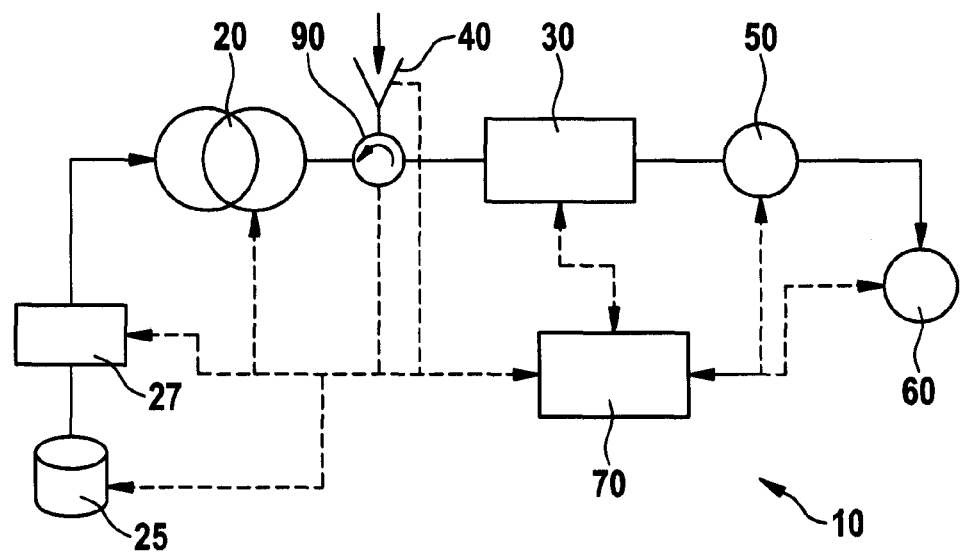
FIG. 24 shows a liquid separation system, in accordance with embodiments of the present invention, for instance used in high performance liquid chromatography (HPLC) and ultra high performance liquid chromatography (UHPLC).

Referring now in greater detail to the drawings, FIG. 24 depicts a general schematic of a liquid separation system 10. A pump 20 receives a mobile phase from a solvent supply 25, typically via a degasser 27, which degasses and thus reduces the amount of dissolved gases in the mobile phase. The pump 20—as a mobile phase drive—drives the mobile phase through a separating device 30 (such as a chromatographic column) comprising a stationary phase. A sampling unit 40 can be provided between the pump 20 and the separating device 30 in order to subject or add (often referred to as sample introduction) a fluidic sample into the mobile phase. The stationary phase of the separating device 30 is adapted for separating compounds of the fluidic sample. A detector 50 is provided for detecting separated compounds of the fluidic sample. A fractionating unit 60 can be provided for outputting separated compounds of the fluidic sample.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a PC or workstation, might be coupled (as indicated by the dotted arrows) to one or more of the devices in the liquid separation system 10 in order to receive information and/or control operation. For example, the data processing unit 70 might control operation of the pump 20 (for instance setting control parameters) and receive therefrom information regarding the actual working conditions (such as output pressure, flow rate, etc. at an outlet of the pump 20). The data processing unit 70 might also control operation of the solvent supply 25 (for instance setting the solvent/s or solvent mixture to be supplied) and/or the degasser 27 (for instance setting control parameters such as vacuum level) and might receive therefrom information regarding the actual working conditions (such as solvent composition supplied over time, flow rate, vacuum level, etc.). The data processing unit 70 might further control operation of the sampling unit 40 (for instance controlling sample injection or synchronization of sample injection with operating conditions of the pump 20). The separating device 30 might also be controlled by the data processing unit 70 (for instance selecting a specific flow path or column, setting operation temperature, etc.), and send—in return—information (for instance operating conditions) to the data processing unit 70. Accordingly, the detector 50 might be controlled by the data processing unit 70 (for instance with respect to spectral or wavelength settings, setting time constants, start/stop data acquisition), and send information (for instance about the detected sample compounds) to the data processing unit 70. The data processing unit 70 might also control operation of the fractionating unit 60 (for instance in conjunction with data received from the detector 50) and provides provide data back.

Reference numeral 90 schematically illustrates a switchable valve which is controllable for selectively enabling or disabling specific fluidic paths within apparatus 10. The switchable valve 90 is not limited to the position between the pump 20 and the separating device 30 and can also be implemented at other positions, depending on the application.

The data processing unit 70 may also process and display measurement data measured by liquid separation system 10 to enable a user to derive technical information from the measurement. Such procedures according to exemplary embodiments will be described in detail in the following. Particularly, methods for evaluating chromatographic results using data correlation and clustering will be explained.

FIG. 1 shows a device 100 (which corresponds to liquid separation system 10 of FIG. 24) for analyzing liquid chromatography measurement data captured by a liquid chromatography measurement device 102 (which corresponds to components 20, 25, 27, 30, 40, 50, 60, 90 of FIG. 24). The liquid chromatography measurement device 102 carries out a plurality of measurements on a fluidic sample to be separated into various fractions. With each measurement, a corresponding data set is captured by the liquid chromatography measurement device 102. Each data set can be indicative of a chromatogram which has a plurality of peaks which will also be called signal features or only features. Each feature indicates the presence of a corresponding fraction or species in the fluidic sample.

After finishing the measurements, the measurement data can be stored in a database 104 for later evaluation.

A fraction identification unit 106 of the device 100 is configured for identifying individual fractions assigned to the features in the chromatogram in different data sets by determining a match with preknown technical information. In other words, certain fractions or components of the fluidic sample which is presently analyzed are expected so that the fraction identification unit 106 can identify peaks in the measurement signals and assign them to the various expected fractions. However, it may also happen that some of the determined features in the measurement spectra cannot be identified, i.e. cannot be assigned to an expected species. This can for instance be caused by impurities in the samples.

Such impurities, which may correspond to undesired or parasitic fractions of the fluidic sample, can then be analyzed by a cluster determining unit 108. The cluster determining unit 108 is configured for determining feature clusters by clustering only the features which could not be assigned to individual fractions by the fraction identification unit 106. For this purpose, the clustering determining unit 108 determines feature clusters by clustering features from different data sets which presumably relate to the same fraction. Examples for a corresponding clustering algorithm, i.e. an algorithm for determining which of the unidentified peaks or features relate to the same fraction or are at least considered to relate to the same fraction will be discussed below in more detail.

The result of the cluster determination is then supplied to a spread determining unit 110. The spread determining unit 110 is configured for determining, for each of the feature clusters individually, a corresponding spread of the features within a respective feature cluster. In other words, a value can be statistically derived which is indicative of a width of the distribution of the individual features within a cluster. In other words, the spread is an indication for the reliability of the clustering (the larger the spread, the lower the reliability).

After having determined a quantitative measure for the spread for each feature cluster individually, a display unit 112 may be fed with the corresponding data and may be configured for determining display data for actually displaying the feature clusters together with the graphical indication of the corresponding spread, for instance on a monitor.

As can be taken by a dashed rectangle in FIG. 1 denoted with reference numeral 114 (which corresponds to component 70 of FIG. 24), units 106, 108, 110, 112 can be realized as a common processor or computer. It is however also possible that each of the units is realized as a separate processor or computer or that some of the units only are realized as a common processor or computer.

An input/output unit 116 is provided for bidirectional communication with the processor 114 as well as the database 104 and the liquid chromatography measurement device 102. Via the input/output unit 116, a user may input instructions to the system, for instance may determine parameters or may define a measurement to be carried out. It is also possible that results of such a measurement or the evaluation is displayed to the user via the input/output unit 16, for instance via a monitor.

Figure 2:
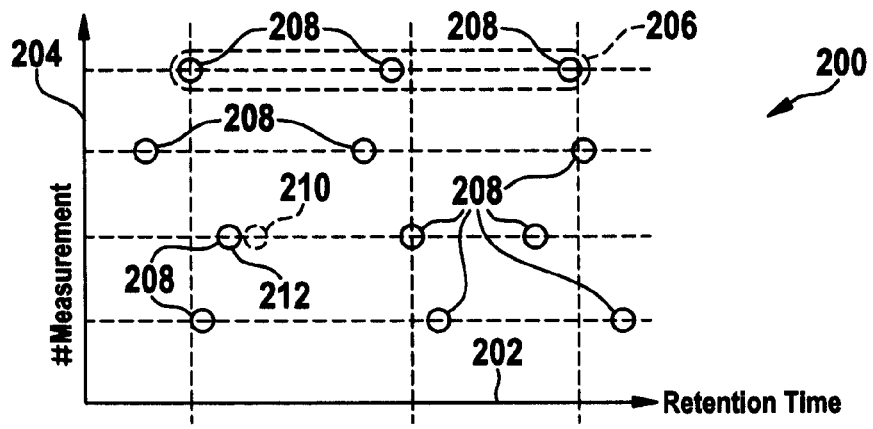
FIG. 2 to FIG. 4 are schemes relating to the execution of a method of processing measurement data having a plurality of data sets and illustrating an algorithm of clustering, calculating a spread and illustrating both together according to an exemplary embodiment of the invention.
Figure 3:
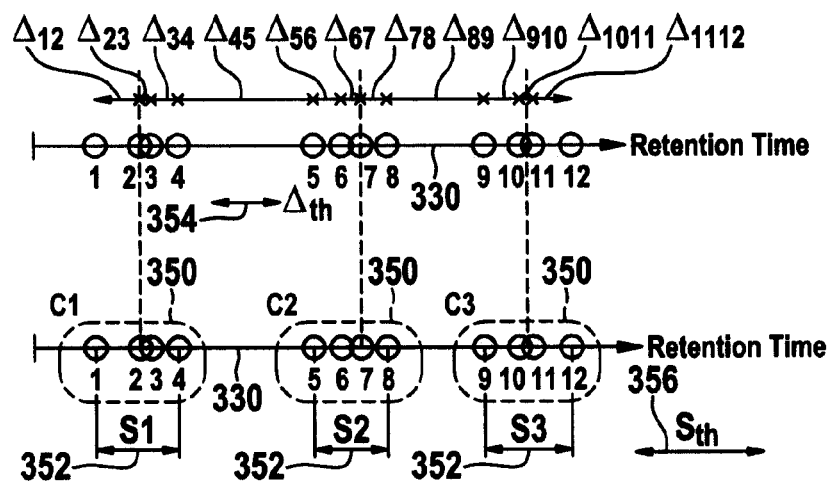
Figure 4:
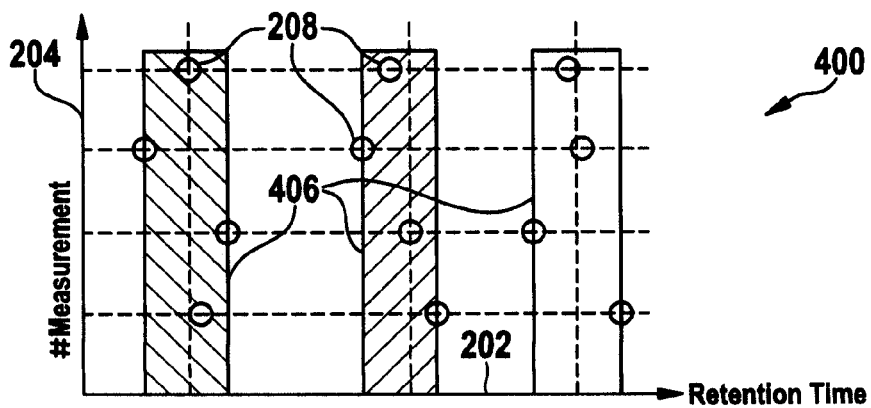

FIG. 2 to FIG. 4 illustrate how the clustering, the spread determination and the graphical display can be performed for the system shown in FIG. 1.

FIG. 2 shows a diagram 200 having an abscissa 202 along which a retention time is plotted according to a liquid or gaseous chromatography measurement. Along an ordinate 204, different measurements performed with the liquid or gaseous chromatography apparatus 102 are illustrated. This means in the shown example that four different measurements are indicated in the diagram of FIG. 2, each illustrated as a corresponding horizontal dotted line. A number of signal features 208 are shown for each measurement in the diagram 200. Hence, each measurement shows a plurality of such features 208. All features 208 relating to one and the same measurement together form a corresponding data set 206, as shown in FIG. 2 as well. Therefore, the four data sets 206 shown in FIG. 2 correspond to the four measurements. In the example of FIG. 2, each data set 206 has three (in this case unidentified) features 208 which are arranged at remarkably different retention times. The following procedure intends to cluster corresponding features 208 which most probably relate to the same fraction of a sample to be separated in the various measurements.

The way how the clustering is performed is shown in FIG. 3 and will be illustrated in the following. Firstly, all unidentified features 208 shown in FIG. 2 are projected on and are ordered quantitatively along an axis 330 shown in FIG. 3 which relates to the abscissa 202 (retention time axis). In other words, all twelve features 208 shown as circles in FIG. 2 are projected onto the abscissa 202 (retention time axis). Hence, the twelve features 208 illustrated as "1", "2", ..., "11", "12" in FIG. 3 are ordered according to their value of the retention time from small to large values. Feature clusters 350 are then determined by clustering all features 208 which fulfill the clustering condition that a difference regarding the value of the retention time between adjacent features 208 of a feature cluster 350 in the ordered representation is below a predetermined threshold value $\Delta_{TH}$ being indicated in FIG. 3 with reference numeral 354. Hence, a distance $\Delta_{12}$ between features "1" and "2" is determined and compared to $\Delta_{TH}$. Since $\Delta_{12}$ is smaller than $\Delta_{TH}$, features "1" and "2" are considered to relate to the same feature cluster 350. Next, features "2" and "3" are analyzed which have a mutual distance $\Delta_{23}$. Since $\Delta_{23}$ is smaller than $\Delta_{TH}$, also features "2" and "3" are considered to relate to the same feature cluster 350. This procedure is continued until it is estimated that the difference $\Delta_{45}$ between features "4" and "5" is larger than $\Delta_{TH}$. Therefore, it is concluded that features "4" and "5" do not relate to the same feature cluster 350. Correspondingly, features "1" to "4" are grouped to form the first feature cluster 350. This procedure is continued so that three feature clusters 350, which are denoted as C1, C2 and C3 in FIG. 3, are identified.

A further consistency check of the cluster formation may be made by comparing a respective width S1, S2 or S3 between the center of the first and the center of the last feature 208 of a respective feature cluster 350 with another threshold value $S_{TH}$ denoted as reference numeral 356. If one of S1, S2 or S3 would be larger than $S_{TH}$, then the corresponding cluster formation would not be considered as reliable and this would be indicated to a user, for instance in the form of an alarm. However, in the present case, each of the cluster formations is considered as consistent. The corresponding values S1, S2 and S3 can be denoted as spreads of corresponding clusters C1, C2 and C3.

FIG. 4 shows a diagram 400 similar to diagram 200. In addition to the information shown in FIG. 2, a bar 406 being indicative for the extension of the corresponding spread S1, S2 or S3 visually shows to the user how reliable the clustering is.

Coming back to FIG. 2, a further feature 210 is shown which relates to the second measurement and has a distance to a preceding feature 212 of less than $\Delta_{TH}$. If such a situation occurs, i.e. that the same measurement shows two features 210, 212 differing less than $\Delta_{TH}$ from one another but relating to the same data set 206, then the later feature 210 is not considered to relate to the same feature cluster 350, because two separable features in the same measurement are indicative of two different fractions and can therefore not be considered to relate to the same fraction for technical considerations. Feature 210 can form a separate cluster with a width or spread of zero, since it is only a single feature.

In the following, referring to FIG. 5 to FIG. 22, a system of forming a graphical illustration of measurement results according to exemplary embodiments of the invention will be explained.

Figure 5:
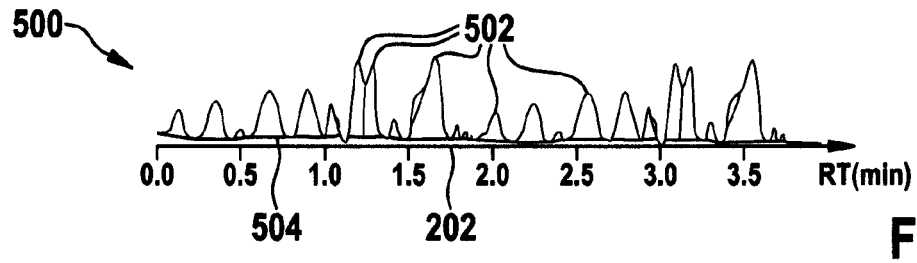
FIG. 5 to FIG. 22 show different images relating to a clustering procedure, spread calculation procedure and a graphic illustration of the latter according to an exemplary embodiment of the invention.

FIG. 5 shows a chromatographic signal 500 illustrating different signal features such as peaks 502 as regions of locally high intensity in a liquid chromatography experiment in dependency of a retention time plotted along abscissa 202. A baseline 504 is shown as well.

Figure 6:
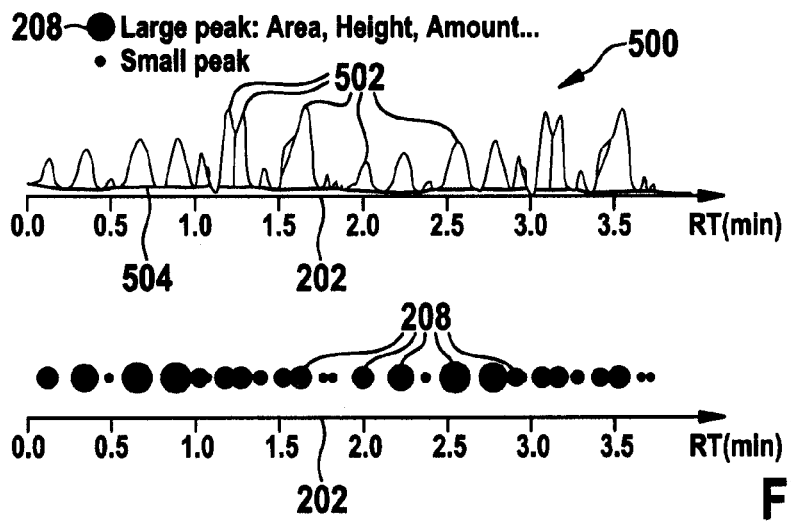

FIG. 6 shows how the chromatographic signal 500 can be transformed into an equivalent bubble diagram in which the individual peaks 502 are displayed as circular structures or features 208. In other words, the area of each feature 208 corresponds to an area under a corresponding peak 502.

Figure 7:
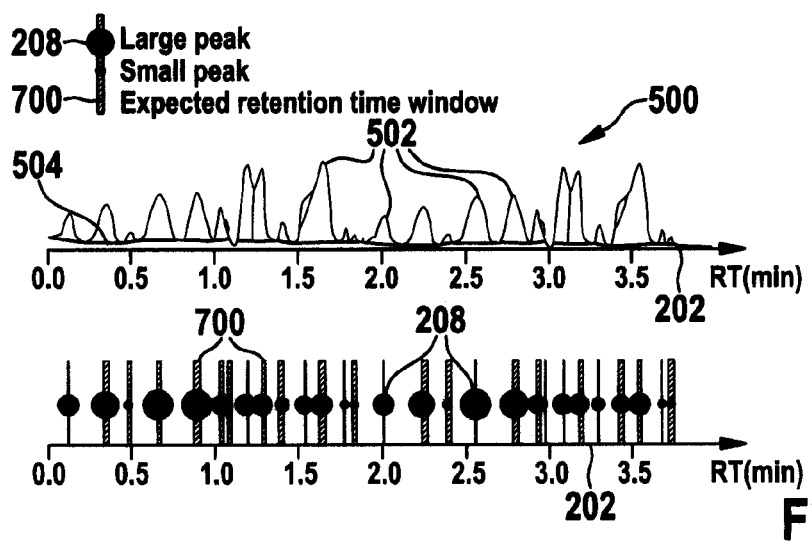

FIG. 7 shows an illustration similar to that of FIG. 6, wherein expected retention time windows—more precisely spreads relating to expected peaks—are illustrated in the form of bars which are denoted with reference numeral 700.

Figure 8:
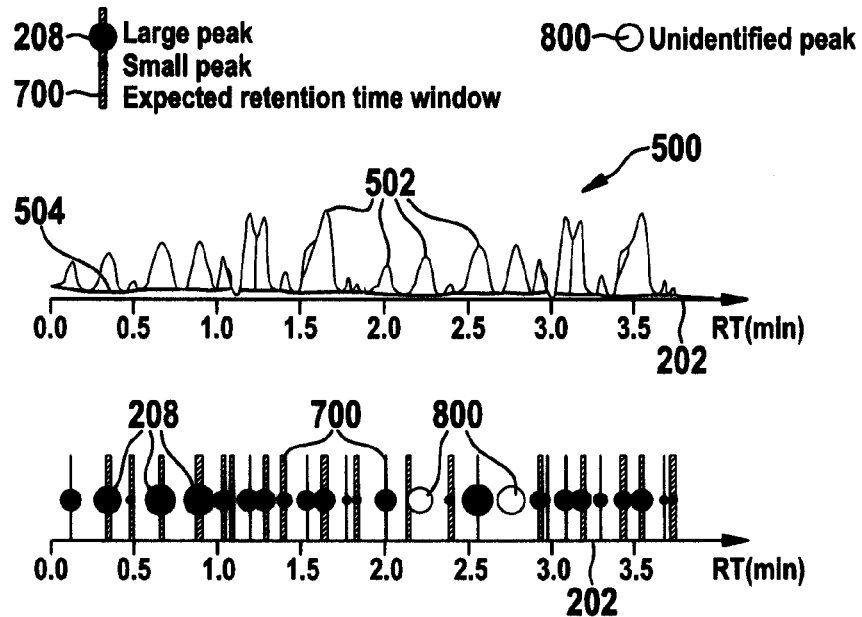

FIG. 8 shows a similar diagram as FIG. 7 with the exception that apart from identified peaks, compare reference numeral 208, also some unidentified peaks are shown which are illustrated by reference numeral 800. An unidentified peak 800 means that the corresponding peak is seen in the chromatographic signal 500, however no such peak would be expected theoretically. Such unidentified peaks 800 may result from impurities in a sample or the like.

Figure 9:
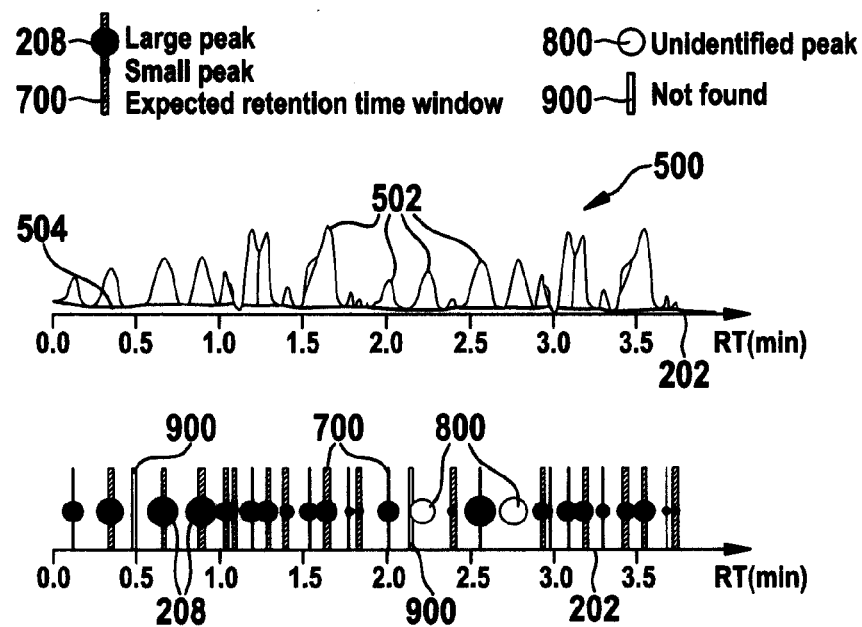

FIG. 9 shows that, apart from the unidentified peaks 800, it may also happen that certain expected peaks are not found in a chromatographic signal 500, as indicated by reference numeral 900. Not found means that there is no local maximum in the chromatographic signal 500 although it would be expected theoretically.

Figure 10:
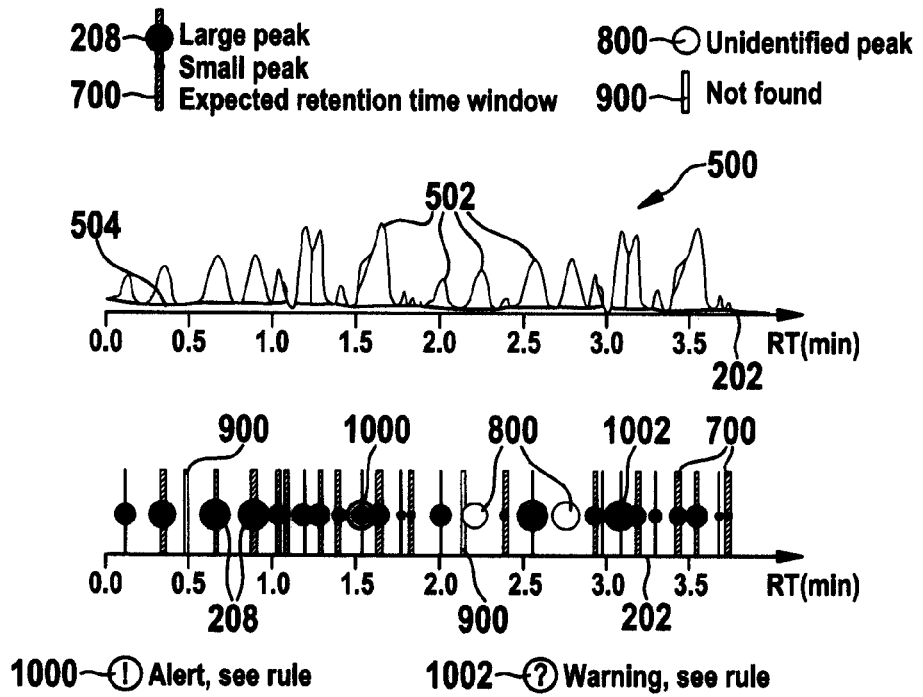

In some events, compare reference numeral 1000 in FIG. 10, an alert may be triggered since an alert rule is violated.

In other cases, see reference numeral 1002, a warning may be output to a user when a warning rule is violated.

Figure 11:
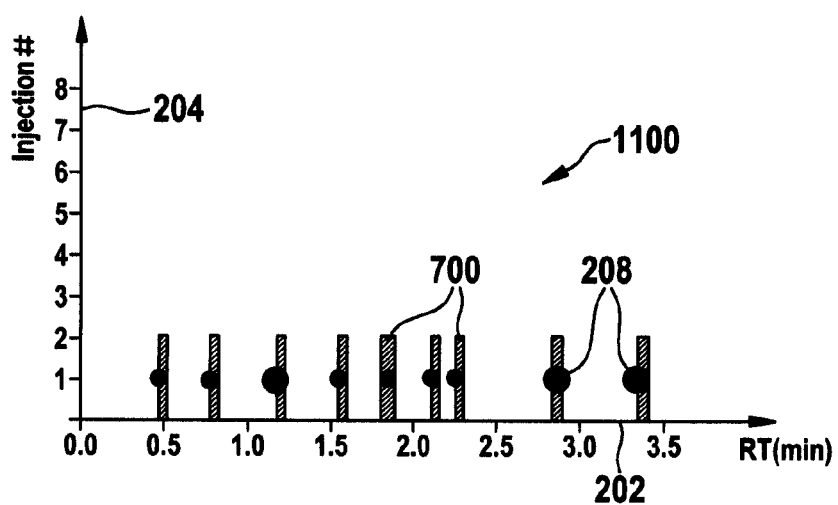

FIG. 11 shows a diagram 1100 in which all peaks of features 208 are shown as bubbles, wherein the size can be proportional to area, height, amount, etc. Vertical bars 700 show the expected retention time window.

Figure 12:
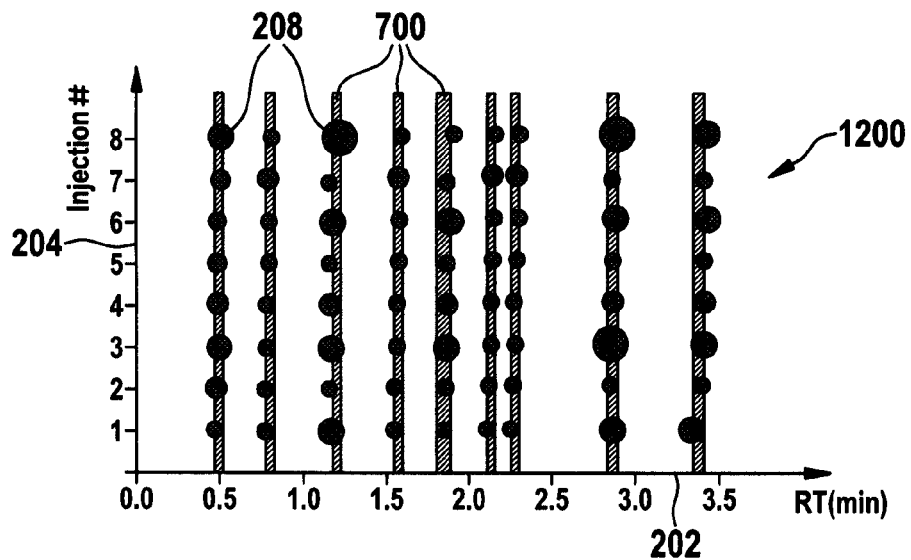

FIG. 12 shows a so-called sequence peak diagram 1200. In this sequence peak diagram 1200, all peaks of features 208 of different injections or measurements are shown as bubbles, wherein the size can be proportional to area, height, amount. The vertical bars 700 show the expected retention time window. Hence, peaks of features 208 from various measurements are illustrated in the sequence peak diagram 1200.

Figure 13:
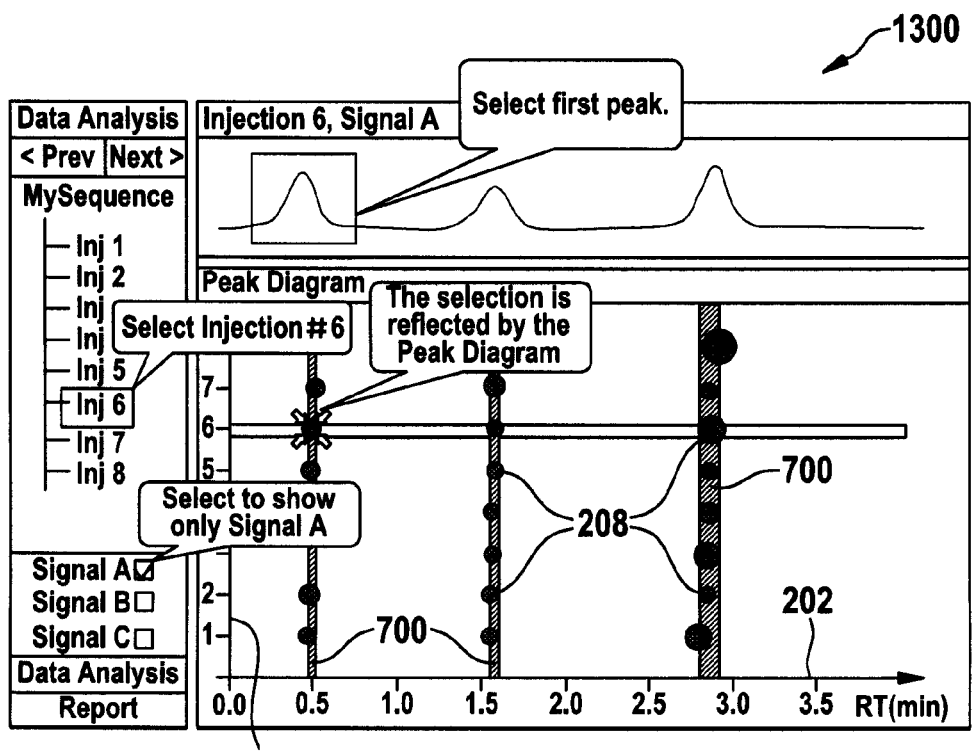

FIG. 13 shows a graphical user interface 1300, in which a user can, in a user-defined manner, design the way of illustrating the various resonances (features 208) and vertical bars 700 in accordance with user preferences.

Figure 14:
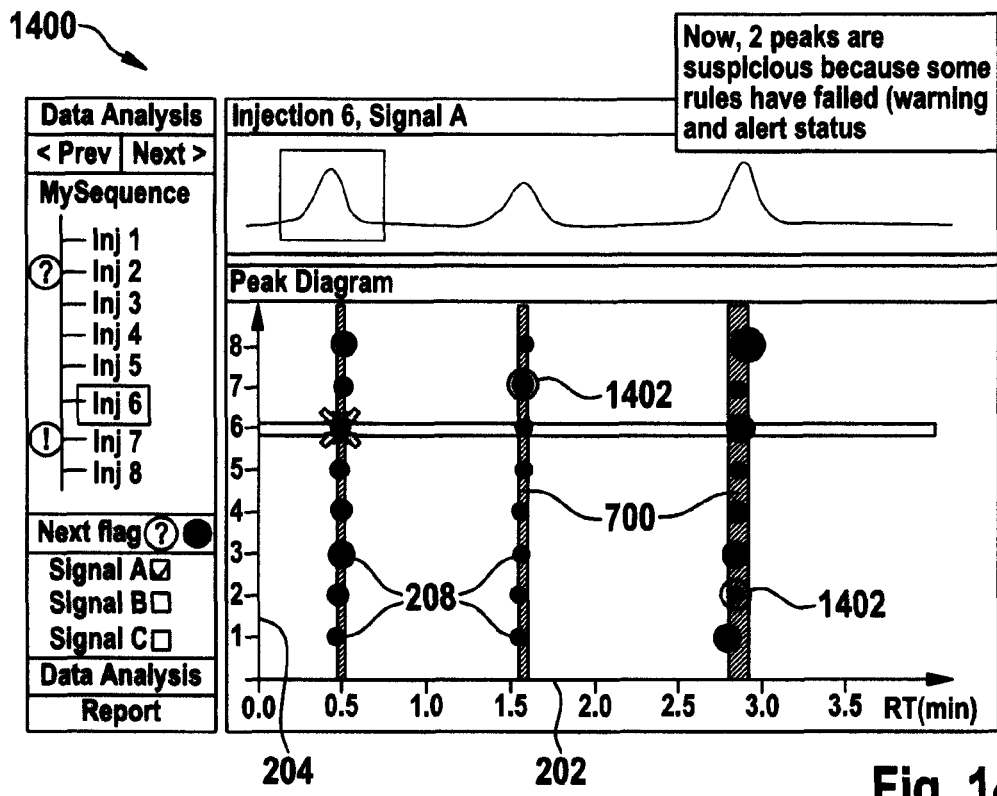

In the graphical user interface 1400 shown in FIG. 14, two peaks 1402 are marked as suspicious, because certain rules have failed (relating to warning and alert status).

Figure 15:
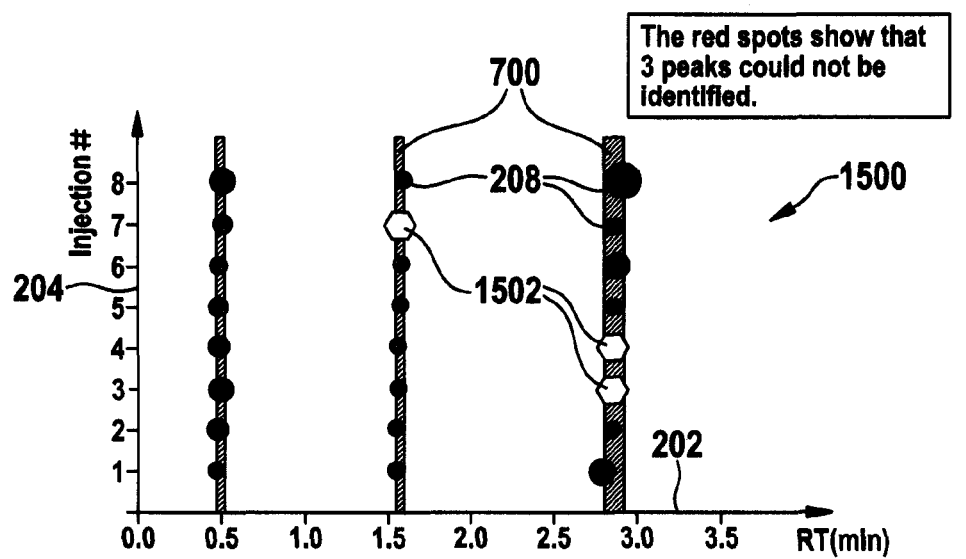

FIG. 15 shows a diagram 1500 in which expected but not found peaks 1502 are shown as well.

Figure 16:
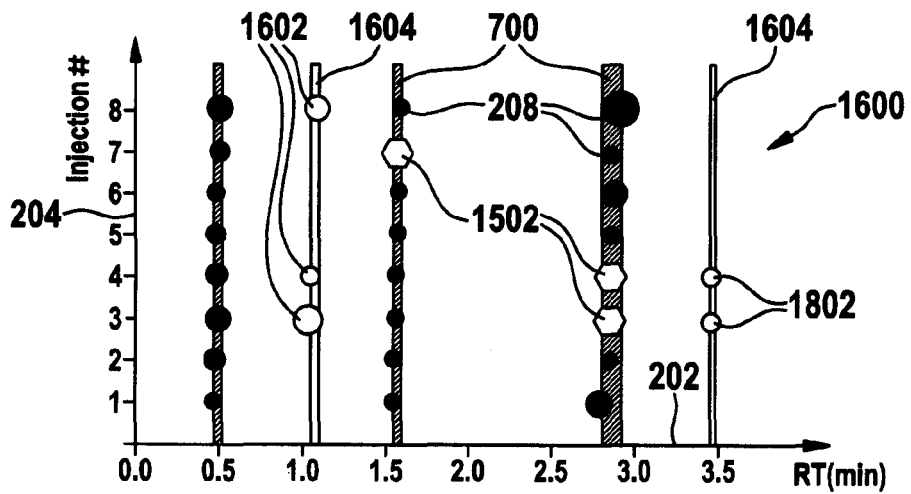

FIG. 16 shows a diagram 1600 which indicates that three injections or measurements show unidentified peaks 1602. As a result of clustering, bands 1604 indicate that these unidentified peaks 1602 could be assigned to two unknown compounds.

Figure 17:
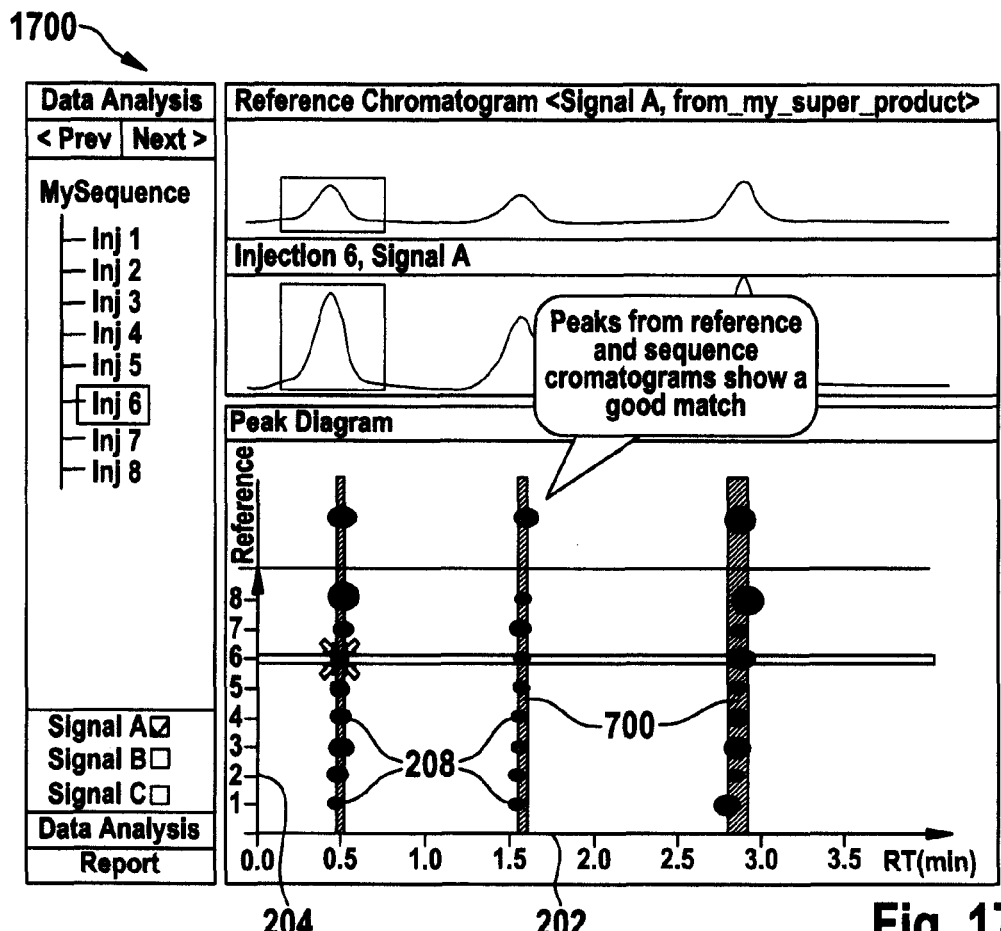

FIG. 17 shows a graphical user interface 1700 in which a comparison against a reference chromatogram is performed, and a proper match is found.

Figure 18:
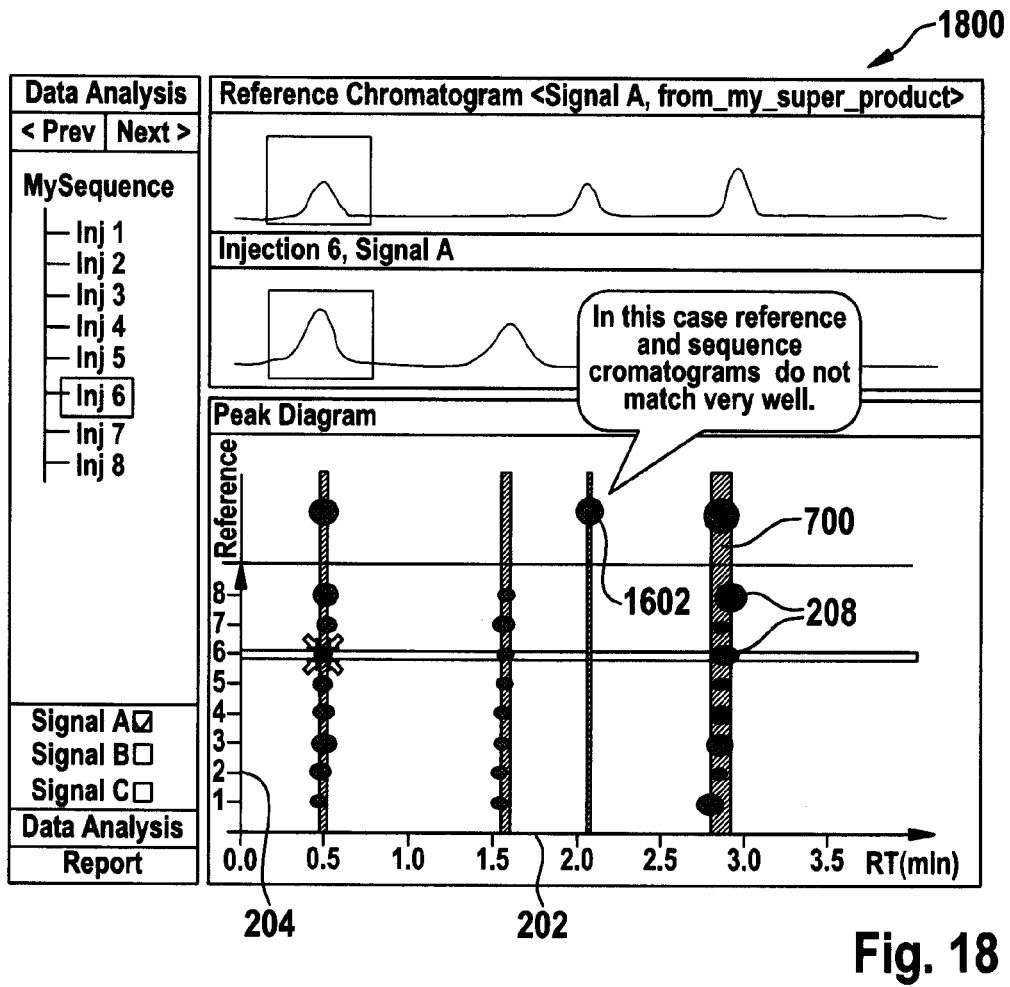

User interface 1800 shown in FIG. 18 shows that at an unidentified peak 1602, reference and sequence chromatograms do not match very well.

Figure 19:
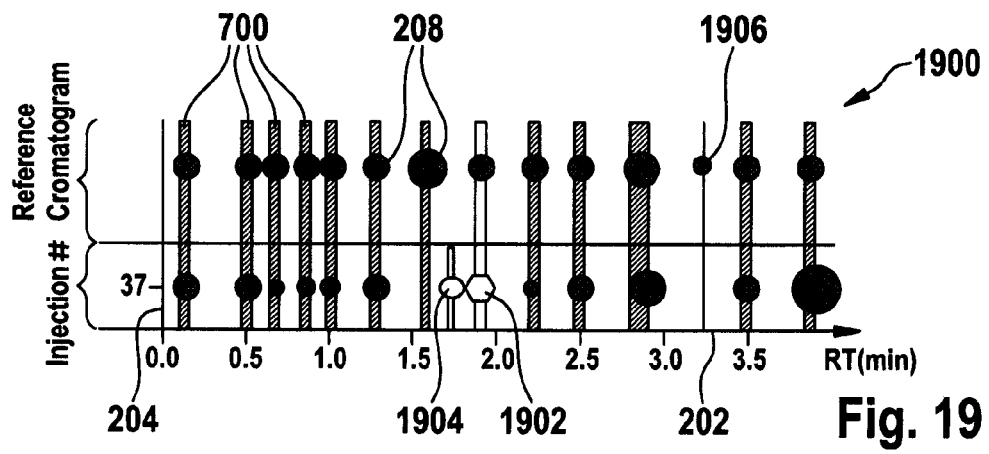

In diagram 1900 in FIG. 19, the sequence chromatogram shows one expected but not found peak 1902, one peak 1904 too many, and one peak 1906 not found.

Figure 20:
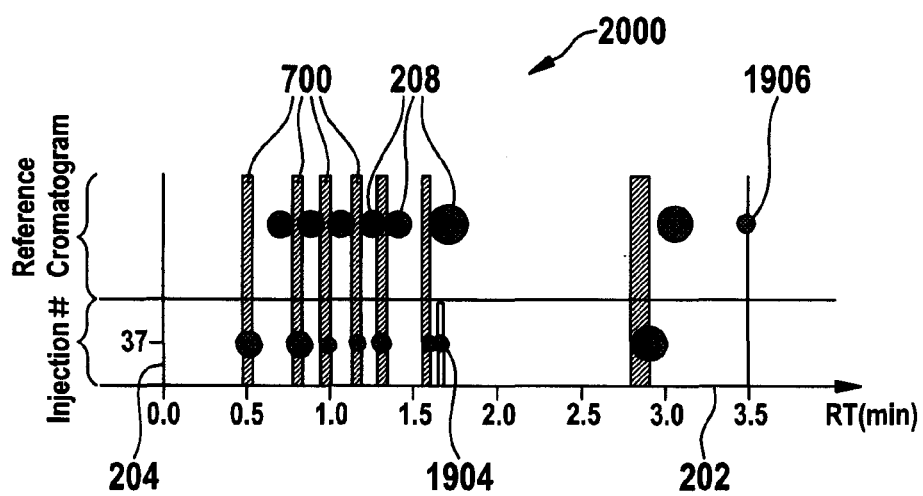
Figure 21:
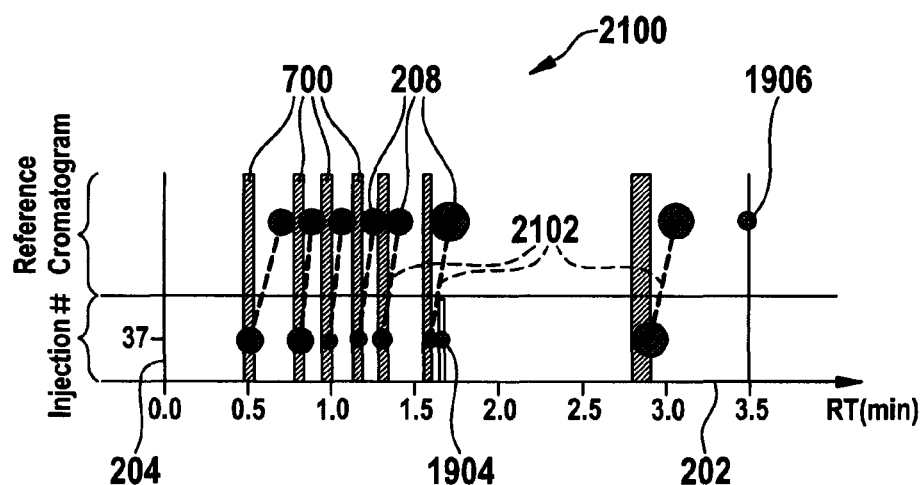

FIG. 20 shows a diagram 2000, in which peaks of a reference and a sequence chromatogram do not match. However, there is some similarity. FIG. 21 shows a diagram 2100 in which the peaks are aligned (see alignment lines 2102).

Figure 22:
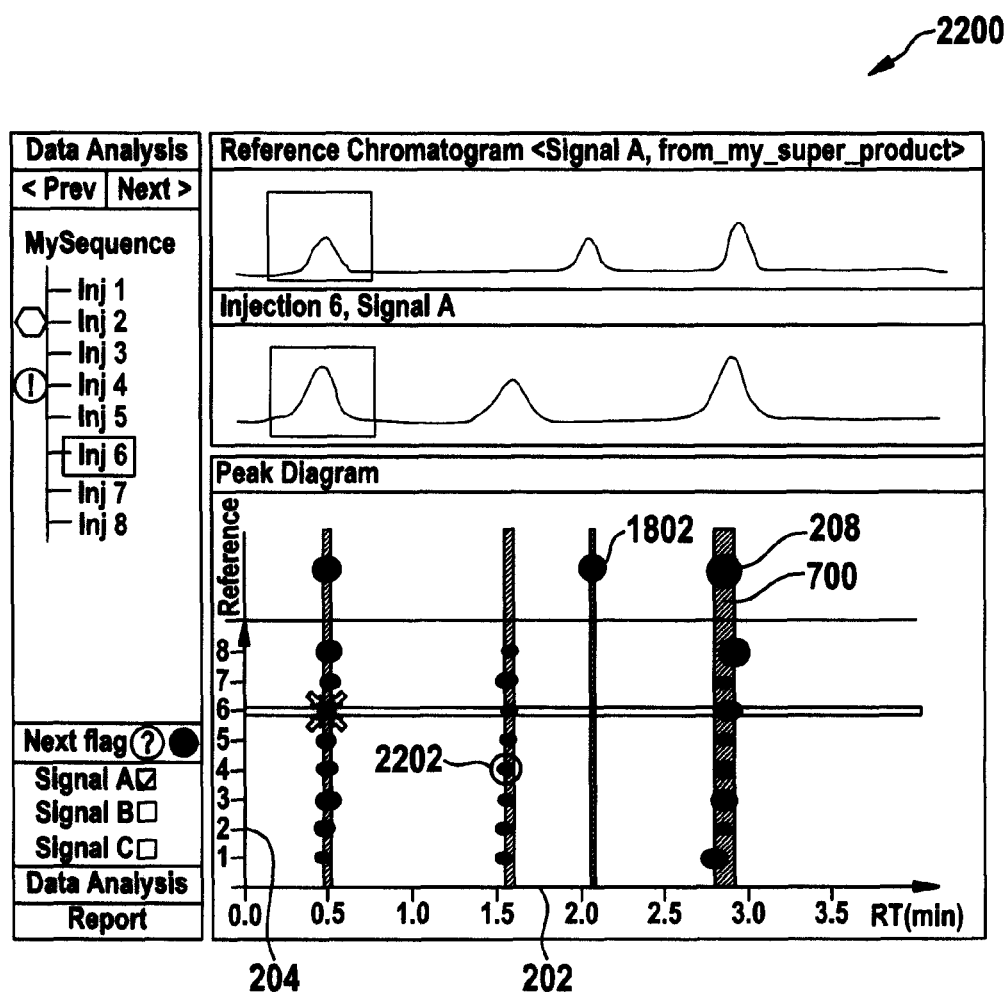

FIG. 22 shows a user interface 2200 in which a suspicious marker 2202 is shown.

Figure 23:
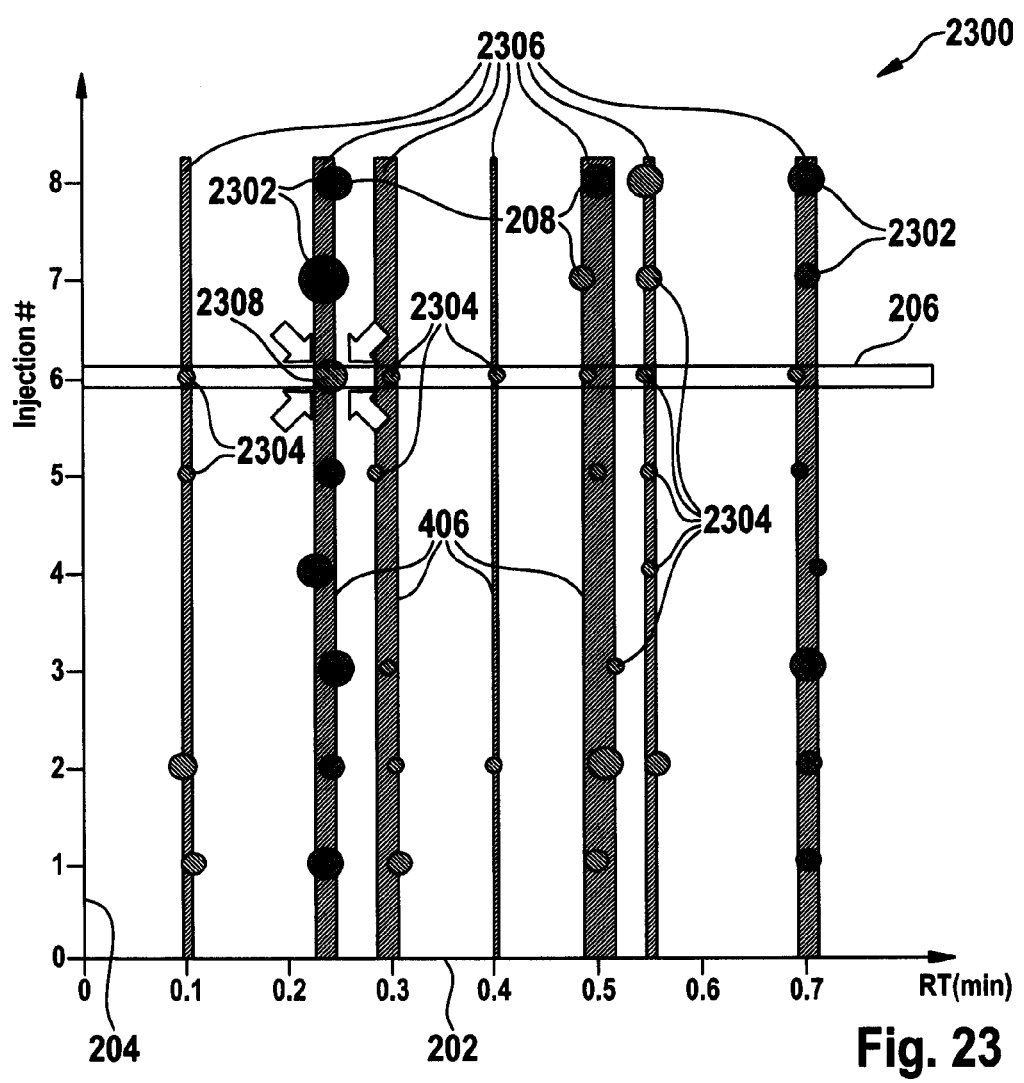
FIG. 23 shows a diagram graphically illustrating different fractions of a fluidic sample separated and being analyzed in terms of cluster formation and spread calculation and illustration.

In FIG. 23, a diagram 2300 can be seen which is similar to diagram 400 and that shows that after clustering of features 208 or peaks the resulting clusters are displayed together with a measure for the spreading.

Unidentified peaks are denoted with reference numeral 2304, identified peaks are denoted with reference numeral 2302, and vertical bands (reference numeral 2306) show formed clusters.

The following description referring to FIG. 23 relates to peak correlation and clustering components. It allows a user to correlate (cluster) unidentified peaks 2304 based on retention times (see abscissa 202). Peaks with retention times that are very close to each other, are assigned to the same cluster. The results are visualized as a graphic control (see FIG. 23) and as table entries (not shown) for further evaluation. The user can control the clustering window size 354 (FIG. 3) which is used for clustering, correct manually a given clustering and apply various filter operations in order to explore the clusters and peaks in detail.

Clustering of peaks can be used when multiple samples show unidentified peaks 2304 and the question rises whether these unidentified peaks 2304 are likely to be caused by the same compound or impurity. The described method will help the user to classify the unidentified peaks 2304 by aligning all those peaks 2304 which show up closely at the same retention time and handle them as new entity, i.e. as a yet unknown compound or impurity.

This may also be useful for developing new methods where retention times of all peaks 2302, 2304 are not known in advance. The found clusters can then be turned into expected retention times for identifying these peaks 2302, 2304.

Depending on the nature of the retention time values clustering will not always lead to a unique solution. Therefore, the user needs an easy way to change the clustering window size 354 (FIG. 3) used for clustering and view in real-time how these manipulations alter the clustering. This will enable the user to select the most meaningful solution.

The user interface for this feature comprises a graphical control showing the positions of all peaks 2302, 2304 and clusters as retention time bands 2306, additional entries for the column table where each column (group of columns) represents data from a specific cluster, and various interactive manipulation means for evaluating the clustered peaks 2302, 2304.

Since expected peaks 2302 are clustered implicitly by data analysis, i.e., the peak identification step, this additional clustering will only be applied to unidentified peaks 2304, in an embodiment.

Therefore, input for clustering is the set of retention times of all unidentified peaks from all injections. Clustering is performed for each signal separately. The only parameter is the clustering window size 354 which specifies the size of the window used to cluster peaks in retention time units (min/sec). If this parameter is not specified the algorithm will determine a default cluster window size from the minimum of non-zero differences of all unidentified peaks.

Output is a collection of clusters (compare reference numeral 350 in FIG. 3). Each cluster lists the retention times, signal and injections which comprise the cluster, as well as the real width of the cluster, calculated as maximum minus minimum of retention times within the cluster.

This clustering feature can be switched on or activated interactively when evaluating peak or compound results. In case clustering is switched on the method will hold the user specified clustering window size 354 or the information to use a default value.

When exploring the clustering interactively the software may vary the clustering window size 354 and calculate the clustering in the background. As a result the relationship of "number of clusters" versus "cluster window size" can be inspected to allow the user to find an optimal clustering window size 354 for the user data. The software will mark the largest clustering window size 354 at which for all injections not more than one peak 2302, 2304 is included in each cluster.

In the case that multiple signals are available the software can optionally collect all identified peaks 2302 from all signals as input to the correlation algorithm. In the correlation result set that peak gets marked which has the largest area from the set of peaks which are from the same injection within the same cluster but from different signals.

In the case multiple detectors are available the signal alignment algorithm may be applied before determining the retention times. This is especially advantageous when combining retention times from all signals as input for the correlation/clustering algorithm.

In case the clustering window size 354 is smaller than the minimum of non-zero differences of all peaks, the number of created clusters is equal to the number of different retention times. In case the clustering window size 354 is larger than the total spread, i.e. maximum minus minimum, of retention times, the number of created clusters equals one. For all other values for the clustering window size 354 the number of resulting clusters is between the two above described values; actually it is a monotonically following step function. The clustering window size 354 is limited by the largest size at which for each injection not more than one peak is included in each cluster.

As mentioned above, FIG. 23 shows the principal layout of the graphical control for presenting all peaks from many injections and their clusters. The X-axis (see reference numeral 202) has the same units as the analyzed signals, i.e. time given in units of min or sec. The Y-axis (see reference numeral 204) shows just the number of injections from which the peaks 2302, 2304 are taken. The position of each peak 2302, 2304 is presented by a circle. The size of the circle represents area, height or any other chosen numerical value of a peak 2302, 2304.

Clusters can be visualized by retention time bands 2306 which may be colored. The presentation of FIG. 23 includes also the identified peaks 2302. The width of the retention time bands 2306 for identified peaks 2302 is just the expected retention time plus/minus the identification window size. The width of the retention time bands 2306 for the unidentified peaks 2304 is chosen in a way that retention times, i.e. center of the circles, of all peaks 2304 belonging to a cluster are within the retention time band 2306. In the case a cluster contains only one peak 2304 then only one colored line is drawn as a cluster retention time band 2306.

Identified peaks 2302 and their clusters may be colored differently from unidentified peaks 2304 and the corresponding clusters. For instance, identified peaks 2302 may be colored blue, unidentified peaks 2304 grey.

A selected injection or measurement is visualized by reference numeral 206; a selected peak may be emphasized by four arrows pointing to the corresponding circle (see reference numeral 2308).

Next, an interactive evaluation of correlated unidentified peaks 2304 will be explained. A prerequisite is that multiple injections are already loaded and integrated; identification can be completed but is not needed. In the case no identification has been done, all peaks 2302, 2304 are handled as unidentified. This might be a useful starting point for developing a new method from scratch.

Assuming the user is evaluating chromatograms and peaks, depending on the user interface layout the user would either switch on the correlation/clustering control or switch to a specific sub-view. The system will immediately calculate the clusters and display the result as a graphic and as added columns to the compound table displaying values for the found clusters. The default is to start with all unidentified peaks from a signal and the cluster window size given by the method: either a specific or the system calculated default value. Using a toolbar, the user can easily switch between different available signals.

In order to determine a proper clustering, the user can display a small popup window that shows the relationship between clustering window size 354 and number of clusters. The user can adapt the clustering window size 354 if needed. There may be a slider on the toolbar which allows the user to evaluate the diagram in real time for varying the clustering window size 354.

Other options are to select which attribute will be shown by the size of the circles that represent each peak 2302, 2304 in the graphic. Possible values are: area, height, peak type, or any numeric value that is an outcome of the rule calculator. The real value is proportional to the area of the circle. The sizes of the circles vary between two predefined values for the minimum and maximum circle.

Further on, the user can suppress peaks 2302, 2304 or full injections (measurements) for clustering. This makes sense when outliers have been identified by the data analysis and these outliers might create values which are not representative for all samples or would distort clustering. Peaks 2302, 2304 or full injections can manually be suppressed interactively for instance by moving the cursor near to a circle. The cursor may change its shape visualizing the possible action to suppress a peak 2302, 2304 or injection or to re-activate a suppressed item.

Other filter options are to show and mark unidentified peaks 2304 that are only detected in some of the injections but not at all, and/or to show and mark ranges of signal where expected peaks 2302 have not identified, i.e. are for any reason not available.

A method according to an embodiment of the invention which includes an algorithm for clustering and correlating data from a series of repeated measurements will be described in detail in the following with an emphasis on the logic of such an algorithm. Integrated with a graphical presentation of the resulting clusters this method allows the user to examine specific features of the measured data in a highly efficient way. The outlined example of peak correlation of chromatographic measurements illustrates advantages of this method, especially in the area of impurity profiling or development of chromatography methods.

The described method allows correlating and clustering any measured numerical feature from a series of repeated measurements. Based on a given small Cluster Window Width (also denoted as predefined threshold value), an algorithm creates clusters of values of a measured feature that are taken from the different measurements of the series. Adjacent values within a cluster are closer to each other than the given window width. However, in an embodiment the chosen Cluster Window Width shall not exceed a size such that more than one data point from a single measurement falls into the same cluster. In general the resulting cluster size may be larger than the starting Cluster Window Width.

The method includes a graphical and tabular presentation of the correlation result. The graphical presentation is a scatter diagram of the measured values. An X-axis relates to the data range of the measured data values and a Y-axis numbers the measurements of the series. The format of the single data points such as color, shape and size can visualize additional features of the data point. A table may be used to list any selected feature of each cluster in a single table column.

In an embodiment, such a system may be applied to chromatographic measurement data. Gas chromatography (GC) and liquid chromatography (LC) are techniques to characterize the chemical composition of gaseous and liquid, i.e. fluidic, samples. During a chromatography run fractions or components (also called compounds) of a mixture are separated, and optionally, identified and quantified. The time it takes the component molecules to travel through the system is called retention time. The result of a chromatographic analysis is a signal (chromatogram) that shows peaks at different retention times corresponding to the different components. In addition, the height or area of the peak can be used to quantify the component in the sample.

One task of data analysis is to allot these peaks, based on the retention time, to components. During method development the retention time of all components of interest are determined and inserted in the method as expected retention time. When running real samples the data analysis part of the system scans the chromatograms for peaks at expected retention times and uses the peak area or height to determine the amount of the components.

Applied to chromatography peak clustering can be used to examine unidentified peaks. For instance, LC or GC analysis is applied to create a series of analyses from different samples taken from a batch of a new synthesized product. In this example the repeated measurements are the recorded chromatograms; the measured feature is the retention time of any unidentified peak within the chromatograms. The described algorithm creates clusters of unidentified peaks from the different chromatograms for which the retention times are very close to each other. One interpretation is that such clusters are caused by unknown compounds which are regarded as impurities or by-products which should not exist at optimal process control. The found clusters are added as "yet unknown" compounds to the compound list.

Some of the diagrams below (for instance FIG. 23) show an exemplary layout of a scatter plot for peak correlation. Not only the unidentified peaks (reference numeral 2304 in FIG. 23) may be drawn, but also the identified peaks (reference numeral 2302 in FIG. 23). Vertical bands (reference numeral 2306 in FIG. 23) show the created clusters, either given by the below described clustering algorithm for unidentified peaks or for expected peaks by peak identification. The width of the bands for identified peaks is just the expected retention time plus/minus the identification window size as specified in the method. The width of the bars or bands for unidentified peaks is chosen in a way that retention times, i.e. center of the circles, of all peaks belonging to a cluster are within the band. The size of circles is chosen to be proportional to the peak area.

This visualization concept may be integrated into a general data analysis software package for chromatographic data. If a user selects any chromatogram or peak for further inspection the related peak will also be highlighted in the scatter diagram.

In addition to displaying all peaks and their correlation the graphical presentation can be used to highlight a variety of peak attributes and to help navigate to suspicious signals. Peaks can be flagged based on the results from applied data evaluation rules.

Next, an exemplary peak clustering algorithm will be described which may be used for the above-described way of illustrating clusters and their spread.

A prerequisite for peak correlation is that multiple signals are loaded and already integrated; identification could have been completed but is not required. In case no identification has been done all peaks are handled as unidentified. This might be a useful starting point for developing a new method from scratch.

The following cluster algorithm may be applied:

```
STEP 1: From each loaded Signal k collect all unidentified Peaks, result:
PeaksInSignal (k)
STEP 2: Merge all PeaksInSinal (k) lists, result: PeakList
STEP 3: Sort PeakList (smallest to largest), result: SortedPeakList
STEP 4: Set ClusterInd = 1, add SortedPeakList(1) to PeakCluster
(ClusterInd)
STEP 5:
FOR i = 2 to NumberOfPeaks in SortedPeakList
    Set k such SortedPeakList (i) is in PeaksInSignal (k)
    IF ((SortedPeakList (i) – SortedPeakList (i–1)) <=
    "Cluster Window Width")
        AND (No Peaks of PeaksInSignal (k) in PeakCluster (ClusterInd))
        Add SortedPeakList (i) to current PeakCluster (ClusterInd)
    ELSE
        Create a new cluster, increment ClusterInd by 1
        Add SortedPeakList (i) to new PeakCluster (ClusterInd)
        END
NEXT i
```

The number of found clusters depends on the size of the Cluster Window Width. A very small width will create many clusters, in extreme as many as unidentified peaks. A helpful tool to preselect an optimal starting value is to show the graph of the number of resulting clusters versus Cluster Window Width.

Embodiments of the invention are capable to assist the chemist to review many peaks from many samples at a glance. Peak clustering and the graphical presentation allows the chemist to check whether all components have been identified and whether additional compounds have been detected. From this diagram, the chemist can directly focus on checking those components that show unexpected behavior.

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

The invention claimed is:

1. A device for analyzing measurement data, the device comprising:
   a processor configured to receive the measurement data, the measurement data comprising a plurality of data sets corresponding to a plurality of respective measurements, wherein:
      the plurality of respective measurements are performed by a fluid separation apparatus in a plurality of respective measurement runs on a plurality of respective fluidic samples;
      each data set comprises a plurality of features indicative of different fractions of one of the plurality of respective fluidic samples;
      each feature represents a combination of a value of a first measurement parameter with a value of a second measurement parameter; and
      the first measurement parameter is selected from the group consisting of: a retention time of a chromatography measurement, a retention volume of a chromatography measurement, and a mass to charge ratio of a coupled chromatography and mass spectroscopy measurement;
   a cluster determining unit configured to determine feature clusters by clustering features from different data sets corresponding to the same fraction based on at least one decision criterion, and further configured to determine, from the feature clusters, a suspicious feature for which a rule for clustering has failed;
   a spread determining unit configured to determine for at least a part of the feature clusters a spread of the features within a respective feature cluster; and
   a display unit configured to display at least the part of the feature clusters together with a graphical indication of the corresponding spread, including displaying the suspicious feature, and further configured to display at least the part of the feature clusters according to a coordinate system comprising a first axis and a second axis, wherein:

the first axis corresponds to the value of the first measurement parameter; and the second axis corresponds to the number of the respective measurement run.

2. The device of claim 1, wherein the cluster determining unit is configured for:

ordering at least a part of the features in accordance with the value of the first measurement parameter, particularly ordering from small to large values; and determining the feature clusters by clustering features to a respective feature cluster which fulfill a clustering condition that a difference regarding the value of the first measurement parameter between adjacent features of a feature cluster in the ordered representation is below a predetermined threshold value.

3. The device of claim 2, wherein the first parameter is retention time, and the predetermined threshold value is a time interval indicative of a difference regarding a retention time of a corresponding fraction in different ones of the measurements.

4. The device of claim 2, wherein the predetermined threshold value is a time interval selected from the group consisting of: a time interval within a range from 0.001 minutes to 0.1 minutes; and a time interval within a range from 0.005 minutes to 0.08 minutes.

5. The device of claim 2, wherein the cluster determining unit is configured for excluding a feature from a feature cluster upon determining that this feature has a value of the first measurement parameter which is larger than a value of the first measurement parameter of another feature of the same data set by less than a predetermined further threshold value.

6. The device of claim 2, wherein the cluster determining unit is configured to determine the feature clusters by clustering all features to a respective feature cluster which fulfill the clustering condition among each other under consideration of a boundary condition that not more than one feature per data set may form part of the same feature cluster.

7. The device of claim 2, wherein the cluster determining unit is configured to determine whether a first and a last of the features in the ordered representation of a feature cluster have a difference regarding the value of the first measurement parameter of more than a predetermined further threshold value, and for triggering an action upon determining that the difference exceeds the predetermined further threshold value.

8. The device of claim 1, wherein the cluster determining unit is configured to determine the feature clusters using a non-recursive algorithm.

9. The device of claim 1, wherein the display unit is configured for displaying, as the graphical indication, a bar having a width corresponding to the respective spread.

10. The device of claim 1, wherein the value of the second measurement parameter for at least the part of the features is displayable encoded by a graphical property of a respective marker representing a corresponding feature in the coordinate system.

11. The device of claim 1, wherein the coordinate system is a Cartesian coordinate system.

12. The device of claim 10, wherein the graphical property is a size of the marker.

13. The device of claim 10, wherein the display unit is configured to display the graphical indication in an overlaying manner with the markers of the features of the corresponding feature cluster.

14. The device of claim 1, wherein the display unit is configured to display the graphical indication extending along the second axis.

15. The device of claim 1, wherein the second measurement parameter is indicative of a detection intensity of a peak of the first measurement parameter.

16. The device of claim 1, comprising a fraction identification unit configured to identify individual fractions assigned to features in different data sets by determining a match with preknown technical information, wherein the cluster determining unit is configured to determine feature clusters by clustering exclusively features which have not been assigned to individual fractions by the fraction identification unit.

17. The device of claim 1, wherein the display unit is configured to display a graphical user interface.

18. The device of claim 1, wherein the measurement data comprises liquid or gaseous chromatography data.

19. The device of claim 1, wherein the measurement data comprises coupled liquid or gaseous chromatography and mass spectroscopy data.

20. The device of claim 1, wherein the measurement data is provided by a measurement device comprising one selected from the group consisting of: a sensor device, a test device for testing a device under test or a substance, a device for chemical, biological and/or pharmaceutical analysis, a fluid separation system configured for separating compounds of a fluid, a capillary electrophoresis device, a liquid chromatography device, a gas chromatography device, an electronic measurement device, and a mass spectroscopy device.

21. A method of analyzing measurement data, the method comprising:

receiving the measurement data, the measurement data comprising a plurality of data sets corresponding to a plurality of respective measurements, wherein:

the plurality of respective measurements are performed by a fluid separation apparatus in a plurality of respective measurement runs on a plurality of respective fluidic samples;

each data set comprises a plurality of features indicative of different fractions of one of the plurality of respective fluidic samples; and each feature represents a combination of a value of a first measurement parameter with a value of a second measurement parameter; and the first measurement parameter is selected from the group consisting of: a retention time of a chromatography measurement, a retention volume of a chromatography measurement, and a mass to charge ratio of a coupled chromatography and mass spectroscopy measurement;

determining feature clusters by clustering features from different data sets corresponding to the same fraction based on at least one decision criterion, and further determining, from the feature clusters, a suspicious feature for which a rule for clustering has failed;

determining for at least a part of the feature clusters a spread of the features within a respective feature cluster; and displaying at least the part of the feature clusters together with a graphical indication of the corresponding spread, including displaying the suspicious feature, and further displaying at least the part of the feature clusters according to a coordinate system comprising a first axis and a second axis, wherein:

the first axis corresponds to the value of the first measurement parameter; and the second axis corresponds to the number of the respective measurement run.

22. The device of claim 1, wherein the plurality of respective measurement runs correspond to a plurality of respective sample injections performed by the fluid separation apparatus.

23. A non-transitory computer-readable medium, comprising instructions stored thereon, that when executed on a processor, control or perform the steps of the method of claim 21.

24. A device for processing measurement data, the device comprising a processor configured to receive the measurement data, the measurement data comprising a plurality of data sets corresponding to a plurality of respective measurements, wherein:

the plurality of respective measurements are performed by a fluid separation apparatus in a plurality of respective measurement runs on a plurality of respective fluidic samples;

each data set comprises a plurality of features indicative of different fractions of one of the plurality of respective fluidic samples;

each feature represents a combination of a value of a first measurement parameter with a value of a second measurement parameter; and the first measurement parameter is selected from the group consisting of: a retention time of a chromatography measurement, a retention volume of a chromatography measurement, and a mass to charge ratio of a coupled chromatography and mass spectroscopy measurement;

a cluster determining unit configured to determine feature clusters by clustering features from different data sets corresponding to the same fraction based on at least one decision criterion, by:

ordering at least a part of the features in accordance with the value of the first measurement parameter; and determining the feature clusters by clustering features to a respective feature cluster in accordance with a clustering condition that a difference regarding the value of the first measurement parameter between adjacent features of a feature cluster in the ordered representation is below a predetermined threshold value, wherein the cluster determining unit is further configured to determine, from the feature clusters, a suspicious feature for which a rule for clustering has failed;

a spread determining unit configured to determine for at least a part of the feature clusters a spread of the features within a respective feature cluster; and a display unit configured to display at least the part of the feature clusters together with a graphical indication of the corresponding spread, including displaying the suspicious feature, and further configured to display at least the part of the feature clusters according to a coordinate system comprising a first axis and a second axis, wherein:

the first axis corresponds to the value of the first measurement parameter; and the second axis corresponds to the number of the respective measurement run.

25. A method of processing measurement data, the method comprising receiving the measurement data, the measurement data comprising a plurality of data sets corresponding to a plurality of respective measurements, wherein:

the plurality of respective measurements are performed by a fluid separation apparatus in a plurality of respective measurement runs on a plurality of respective fluidic samples;

each data set comprises a plurality of features indicative of different fractions of one of the plurality of respective fluidic samples; and each feature represents a combination of a value of a first measurement parameter with a value of a second measurement parameter; and the first measurement parameter is selected from the group consisting of: a retention time of a chromatography measurement, a retention volume of a chromatography measurement, and a mass to charge ratio of a coupled chromatography and mass spectroscopy measurement;

determining feature clusters by clustering features from different data sets corresponding to the same fraction based on at least one decision criterion, by:

ordering at least a part of the features in accordance with the value of the first measurement parameter; and determining the feature clusters by clustering features to a respective feature cluster in accordance with a clustering condition that a difference regarding the value of the first measurement parameter between adjacent features of a feature cluster in the ordered representation is below a predetermined threshold value;

further determining, from the feature clusters, a suspicious feature for which a rule for clustering has failed;

determining for at least a part of the feature clusters a spread of the features within a respective feature cluster; and displaying at least the part of the feature clusters together with a graphical indication of the corresponding spread, including displaying the suspicious feature, and further displaying at least the part of the feature clusters according to a coordinate system comprising a first axis and a second axis, wherein:

the first axis corresponds to the value of the first measurement parameter; and the second axis corresponds to the number of the respective measurement run.

* * * * *